US008303590B2

(12) United States Patent
Elghazaly et al.

(10) Patent No.: US 8,303,590 B2
(45) Date of Patent: Nov. 6, 2012

(54) LOCKABLE INTRAMEDULLARY FIXATION DEVICE

(75) Inventors: Timothy M. Elghazaly, Piscataway, NJ (US); Stephen B. Walulik, Stewartsville, NJ (US); Kirk J. Bailey, Blairstown, NJ (US); Philip H. Frank, Maplewood, NJ (US); Joseph M. O'Reilly, South Plainfield, NJ (US)

(73) Assignee: EBI, LLC, Parsippany, NJ (US)

( * ) Notice: Subject to any disclaimer, the term of this patent is extended or adjusted under 35 U.S.C. 154(b) by 1099 days.

(21) Appl. No.: 11/627,575

(22) Filed: Jan. 26, 2007

(65) Prior Publication Data
US 2008/0183171 A1 Jul. 31, 2008

(51) Int. Cl.
*A61B 17/72* (2006.01)

(52) U.S. Cl. .......................................... 606/64
(58) Field of Classification Search .............. 606/62–68
See application file for complete search history.

(56) References Cited

U.S. PATENT DOCUMENTS

| | | | |
|---|---|---|---|
| 2,068,152 A | 1/1937 | Rowe | |
| 2,201,674 A | 5/1940 | Rowe et al. | |
| 2,222,156 A | 11/1940 | Rowe | |
| 2,725,915 A * | 12/1955 | Johnson | 411/302 |
| 2,789,276 A | 4/1957 | Hummel | |
| 2,913,031 A * | 11/1959 | McKay et al. | 411/304 |
| 3,308,865 A * | 3/1967 | Raichelson et al. | 411/302 |
| 3,501,993 A | 3/1970 | Swenson | |
| 3,709,218 A | 1/1973 | Halloran | |
| 3,836,941 A | 9/1974 | Izraeli | |
| 3,990,438 A * | 11/1976 | Pritchard | 606/311 |
| 4,354,399 A | 10/1982 | Katayama et al. | |
| 4,450,835 A | 5/1984 | Asnis et al. | |
| 4,622,959 A * | 11/1986 | Marcus | 606/64 |
| 4,710,075 A | 12/1987 | Davison | |
| 4,733,661 A | 3/1988 | Palestrant | |
| 4,756,307 A | 7/1988 | Crowninshield | |
| 4,776,330 A | 10/1988 | Chapman et al. | |
| 4,827,917 A | 5/1989 | Brumfield | |
| 4,828,562 A | 5/1989 | Kenna | |
| 4,858,602 A | 8/1989 | Seidel et al. | |
| 4,875,475 A | 10/1989 | Comte et al. | |
| 4,895,572 A | 1/1990 | Chernoff | |

(Continued)

FOREIGN PATENT DOCUMENTS

DE 69511549 T2 3/2000

(Continued)

OTHER PUBLICATIONS

Halder, S.C., The Gamma Nail for Peritrochanteric Fractures, The Journal of Bone and Joint Surgery, May 1992, pp. 340-344, vol. 74-B, No. 3, 1992 British Editorial Society of Bone and Joint Surgery.

(Continued)

*Primary Examiner* — Alvin Stewart
*Assistant Examiner* — Jerry Cumberledge
(74) *Attorney, Agent, or Firm* — Harness, Dickey

(57) ABSTRACT

An orthopedic device can include an intramedullary nail and an insert telescopically received in the intramedullary nail. The insert includes at least two guiding bores for corresponding bone fasteners that can be locked at an angle to the intramedullary nail. A locking set screw can be coupled to the insert and move the insert to a position that locks the bone fasteners to the nail.

24 Claims, 22 Drawing Sheets

U.S. PATENT DOCUMENTS

| | | | |
|---|---|---|---|
| 5,034,013 A | 7/1991 | Kyle et al. | |
| 5,041,114 A | 8/1991 | Chapman et al. | |
| 5,041,115 A | 8/1991 | Frigg et al. | |
| 5,066,296 A | 11/1991 | Chapman et al. | |
| 5,112,333 A | 5/1992 | Fixel | |
| 5,190,544 A | 3/1993 | Chapman et al. | |
| 5,295,991 A | 3/1994 | Frigg | |
| 5,383,525 A * | 1/1995 | Daly et al. | 175/57 |
| 5,505,734 A | 4/1996 | Caniggia et al. | |
| 5,549,610 A | 8/1996 | Russell et al. | |
| 5,653,709 A * | 8/1997 | Frigg | 606/64 |
| 5,658,287 A * | 8/1997 | Hofmann et al. | 606/63 |
| 5,690,515 A | 11/1997 | Cipolla | |
| 5,697,930 A | 12/1997 | Itoman et al. | |
| 5,704,939 A | 1/1998 | Justin | |
| 5,728,128 A | 3/1998 | Crickenberger et al. | |
| 5,779,705 A | 7/1998 | Matthews | |
| 5,935,127 A | 8/1999 | Border | |
| 6,004,324 A | 12/1999 | Gahr et al. | |
| 6,010,506 A | 1/2000 | Gosney et al. | |
| 6,019,761 A | 2/2000 | Gustilo | |
| 6,036,696 A | 3/2000 | Lambrecht et al. | |
| 6,080,024 A | 6/2000 | Miller et al. | |
| 6,106,528 A * | 8/2000 | Durham et al. | 606/64 |
| 6,120,504 A | 9/2000 | Brumback et al. | |
| 6,168,595 B1 | 1/2001 | Durham et al. | |
| 6,214,013 B1 | 4/2001 | Lambrecht et al. | |
| 6,221,074 B1 * | 4/2001 | Cole et al. | 606/62 |
| 6,228,086 B1 * | 5/2001 | Wahl et al. | 606/67 |
| 6,296,645 B1 | 10/2001 | Hover et al. | |
| 6,402,753 B1 | 6/2002 | Cole et al. | |
| 6,406,477 B1 | 6/2002 | Fujiwara et al. | |
| 6,461,360 B1 | 10/2002 | Adam | |
| 6,520,969 B2 | 2/2003 | Lambrecht et al. | |
| 6,547,791 B1 | 4/2003 | Buhren et al. | |
| 6,562,042 B2 | 5/2003 | Nelson | |
| 6,569,165 B2 * | 5/2003 | Wahl et al. | 606/67 |
| 6,579,294 B2 | 6/2003 | Robioneck | |
| 6,648,889 B2 | 11/2003 | Bramlet et al. | |
| 6,702,816 B2 * | 3/2004 | Buhler | 606/62 |
| 6,709,436 B1 | 3/2004 | Hover et al. | |
| 6,786,908 B2 | 9/2004 | Hover et al. | |
| 6,808,527 B2 | 10/2004 | Lower et al. | |
| 6,835,197 B2 | 12/2004 | Roth et al. | |
| 6,921,400 B2 | 7/2005 | Sohngen | |
| 6,926,719 B2 | 8/2005 | Sohngen et al. | |
| 6,932,819 B2 | 8/2005 | Wahl et al. | |
| 6,960,212 B2 | 11/2005 | Richelsoph et al. | |
| 7,018,380 B2 | 3/2006 | Cole | |
| 7,041,104 B1 | 5/2006 | Cole et al. | |
| 7,182,765 B2 | 2/2007 | Roth et al. | |
| 7,306,600 B2 | 12/2007 | Roth et al. | |
| 7,455,673 B2 | 11/2008 | Gotfried | |
| 7,527,627 B2 * | 5/2009 | Ferrante et al. | 606/64 |
| 7,763,021 B2 * | 7/2010 | Cole et al. | 606/64 |
| 2002/0133156 A1 | 9/2002 | Cole | |
| 2002/0156473 A1 * | 10/2002 | Bramlet et al. | 606/62 |
| 2003/0114855 A1 | 6/2003 | Wahl et al. | |
| 2003/0195515 A1 | 10/2003 | Sohngen | |
| 2004/0138663 A1 * | 7/2004 | Kosashvili et al. | 606/62 |
| 2004/0158252 A1 * | 8/2004 | Prager et al. | 606/72 |
| 2004/0260307 A1 | 12/2004 | Zander | |
| 2005/0010223 A1 * | 1/2005 | Gotfried | 606/62 |
| 2005/0069397 A1 | 3/2005 | Shavit et al. | |
| 2005/0070903 A1 | 3/2005 | Roth et al. | |
| 2005/0101958 A1 | 5/2005 | Adam | |
| 2005/0107790 A1 | 5/2005 | Qian | |
| 2005/0143739 A1 * | 6/2005 | Shinjo et al. | 606/62 |
| 2005/0203510 A1 * | 9/2005 | Sohngen | 606/60 |
| 2005/0273103 A1 | 12/2005 | Wahl et al. | |
| 2006/0111716 A1 * | 5/2006 | Schlienger et al. | 606/64 |
| 2006/0111717 A1 * | 5/2006 | Saueressig et al. | 606/64 |
| 2006/0122600 A1 | 6/2006 | Cole | |
| 2006/0149264 A1 | 7/2006 | Castaneda et al. | |
| 2006/0173457 A1 * | 8/2006 | Tornier | 606/62 |
| 2006/0200141 A1 * | 9/2006 | Janna et al. | 606/62 |
| 2006/0200160 A1 | 9/2006 | Border et al. | |
| 2006/0235395 A1 | 10/2006 | Frigg et al. | |
| 2007/0100343 A1 | 5/2007 | Cole et al. | |
| 2007/0233100 A1 | 10/2007 | Metzinger | |
| 2008/0221577 A1 | 9/2008 | Elghazaly | |
| 2008/0294164 A1 | 11/2008 | Frank et al. | |
| 2008/0300637 A1 | 12/2008 | Austin et al. | |
| 2009/0048600 A1 | 2/2009 | Matityahu et al. | |

FOREIGN PATENT DOCUMENTS

| | | |
|---|---|---|
| EP | 0764006 A1 | 3/1997 |
| EP | 1557131 | 7/2005 |
| ES | 2134479 T3 | 10/1999 |
| GB | 2290478 A | 1/1996 |
| WO | 9534248 A1 | 12/1995 |
| WO | WO-0143652 A | 6/2001 |
| WO | WO-03061495 | 7/2003 |
| WO | WO-03094763 | 11/2003 |
| WO | WO-2004082493 | 9/2004 |
| WO | WO-2004100810 A1 | 11/2004 |
| WO | WO-2006107222 A2 | 10/2006 |
| WO | WO-2007038560 A1 | 4/2007 |

OTHER PUBLICATIONS

Damron, Timothy A., et al., Long Gamma Nail Stabilization of Pathologic and Impending Pathologic Femur Fractures, the University of Pennsylvania Orthopaedic Journal, 1999, pp. 13-20, vol. 12.

Synthes®, The Titanium Femoral Nail System, Solid and Cannulated Nails, Technique Guide, ©1996 Synthes (USA).

Stryker® Trauma, One Shot™ Device, Gamma® Locking Nail Instruments, Opera Tive Technique, ©2000 Stryker Corporation.

Stryker® Trauma, Gamma3™ The Compact Version of the Gamma™ Nail System, Operative Technique, Hip Fracture System, Trochanteric and Long Nails, Brochure, © 2004 Stryker, Printed in USA.

PCT International Search Report and The Written Opinion of the International Searching Authority for PCT/US2008/000568 mailed Jun. 2, 2008.

PCT international Preliminary Report on Patentability (Chapter 1 of the Patent Cooperation Treaty) with PCT Written Opinion of the International Searching Authority for PCT/US2008/000568 mailed Aug. 6, 2009.

Non-Final Office Action for U.S. Appl. No. 12/117,765, mailed Mar. 17, 2011.

Non-Final Office Action for U.S. Appl. No. 12/183,142, mailed Mar. 16, 2011.

Office Action regarding European Patent Application No. 08 724 539.5—2310, dated Apr. 19, 2011.

First Office Action regarding Chinese Patent Application No. 200910137547.5, dated Jan. 26, 2011. English translation provided by Unitalen Attorneys at Law.

First Office Action regarding Chinese Patent Application No. 200880006581.2, dated Jan. 30, 2011. English translation provided by Unitalen Attorenys at Law.

Chinese First Office Action Dated Aug. 17, 2011; Machine Translation provided by Unitalen.

Final Office Action for U.S. Appl. No. 12/117,765 Mailed Sep. 13, 2011.

Final Office Action for U.S. Appl. No. 12/183,142 Mailed Sep. 6, 2011.

Second Chinese Office Action for Patent Application No. 200910137547.5 Mailed Dec. 16, 2011 (English Translation provided by Peksung Intellectual Property Ltd.).

First Official Report for Australian Patent Application No. 2008211285, dated Jul. 4, 2012.

* cited by examiner

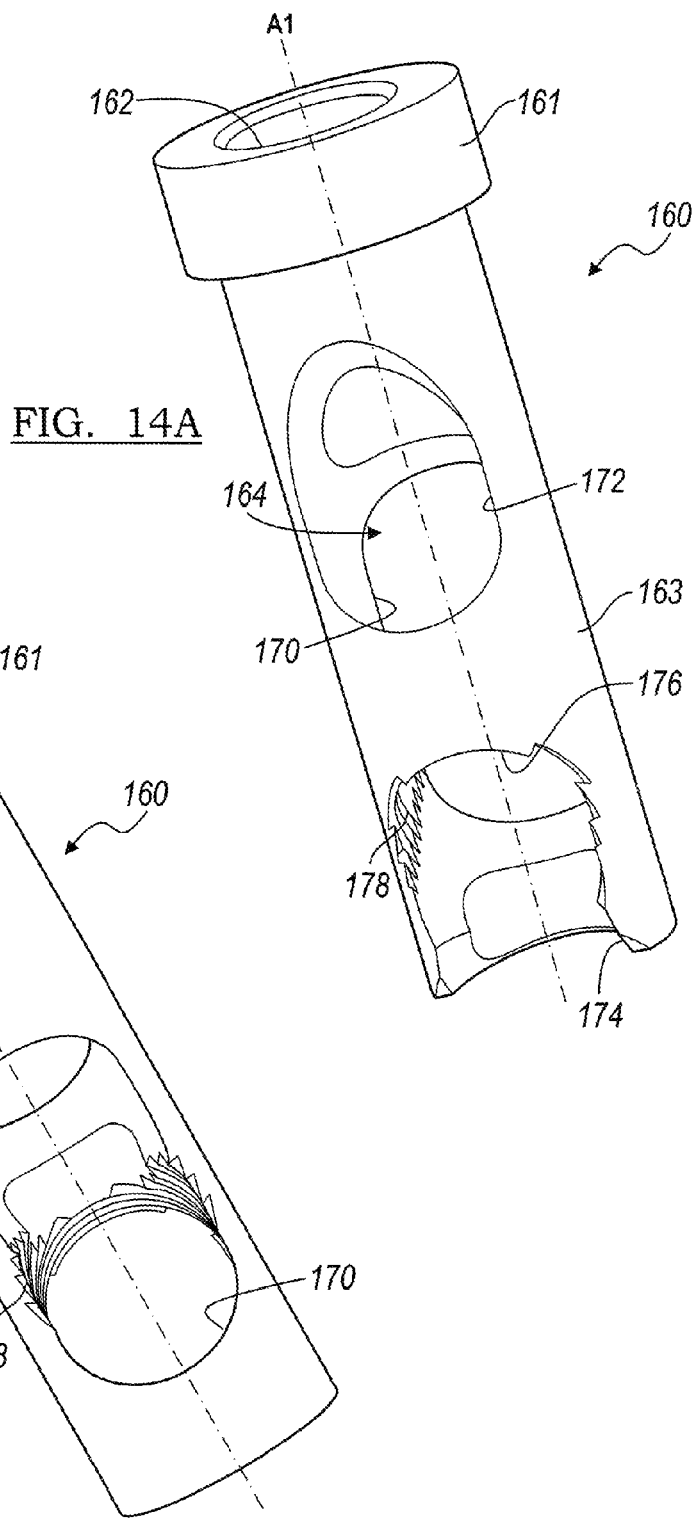

LOCKABLE INTRAMEDULLARY FIXATION DEVICE

INTRODUCTION

Different nailing systems and associated instruments are known for the fixation of fractures of the femur, such as shaft fractures, subtrochanteric fractures, intertrochanteric fractures, neck fractures and combinations thereof, as well as for reconstruction of the femur following tumor resection or other surgery.

The present teachings provide for versatile and effective internal fixation devices that can be used for internal fixation of long bones.

SUMMARY

The present teachings provide an orthopedic device that includes an intramedullary implant defining a longitudinal bore, and a cannulated movable member receivable within the longitudinal bore and telescopically movable relative to the longitudinal bore. The movable member defines a plurality of guiding bores for bone fasteners, and is movable between a fastener engagement position and a fastener disengagement position. The guiding bores can be at an angle relative to the longitudinal bore of the intramedullary implant.

In another aspect, the present teachings provide an orthopedic device that includes an intramedullary implant defining a longitudinal bore and a plurality of fastener bores inclined relative to the longitudinal bore, a plurality of bone fasteners receivable in corresponding fastener bores, and a securing device. The securing device can move telescopically within the longitudinal bore between a first position that engages at least two bone fasteners to the intramedullary implant, and a second position that disengages the two bone fasteners from to the intramedullary implant.

In yet another aspect, the present teachings provide an intramedullary implant defining a longitudinal bore and at least first and second fastener bores inclined relative to the longitudinal bore. The orthopedic device can further include at least first and second of bone fasteners receivable in the corresponding first and second fastener bores, a movable member and a locking member. The movable member defines at least first and second guiding bores for receiving the first and second fasteners, and can telescopically move within the longitudinal bore between a first position that engages the first and second bone fasteners to the intramedullary implant, and a second position that disengages the first and second bone fasteners from to the intramedullary implant, the movable member. The locking member can have an externally threaded portion threadably engageable to a threaded portion of the longitudinal bore, and a resilient portion couplable to the movable member.

The present teaching further provide an orthopedic device that includes an intramedullary implant defining a longitudinal bore, at least one bone fastener, and a securing device. The securing device is movable within the longitudinal bore between a locked position that engages the at least one bone fastener to the intramedullary implant, and an unlocked position that disengages the at least one bone fastener from to the intramedullary implant. The securing device includes at least one guiding bore threadably engageable or threadably disengageable with the at least one bone fastener while the securing device is in the locked position.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 14A and 14B are perspective views of an insert for the fixation devices of FIGS. 10 and 12;

DESCRIPTION OF VARIOUS ASPECTS

Figure 1:
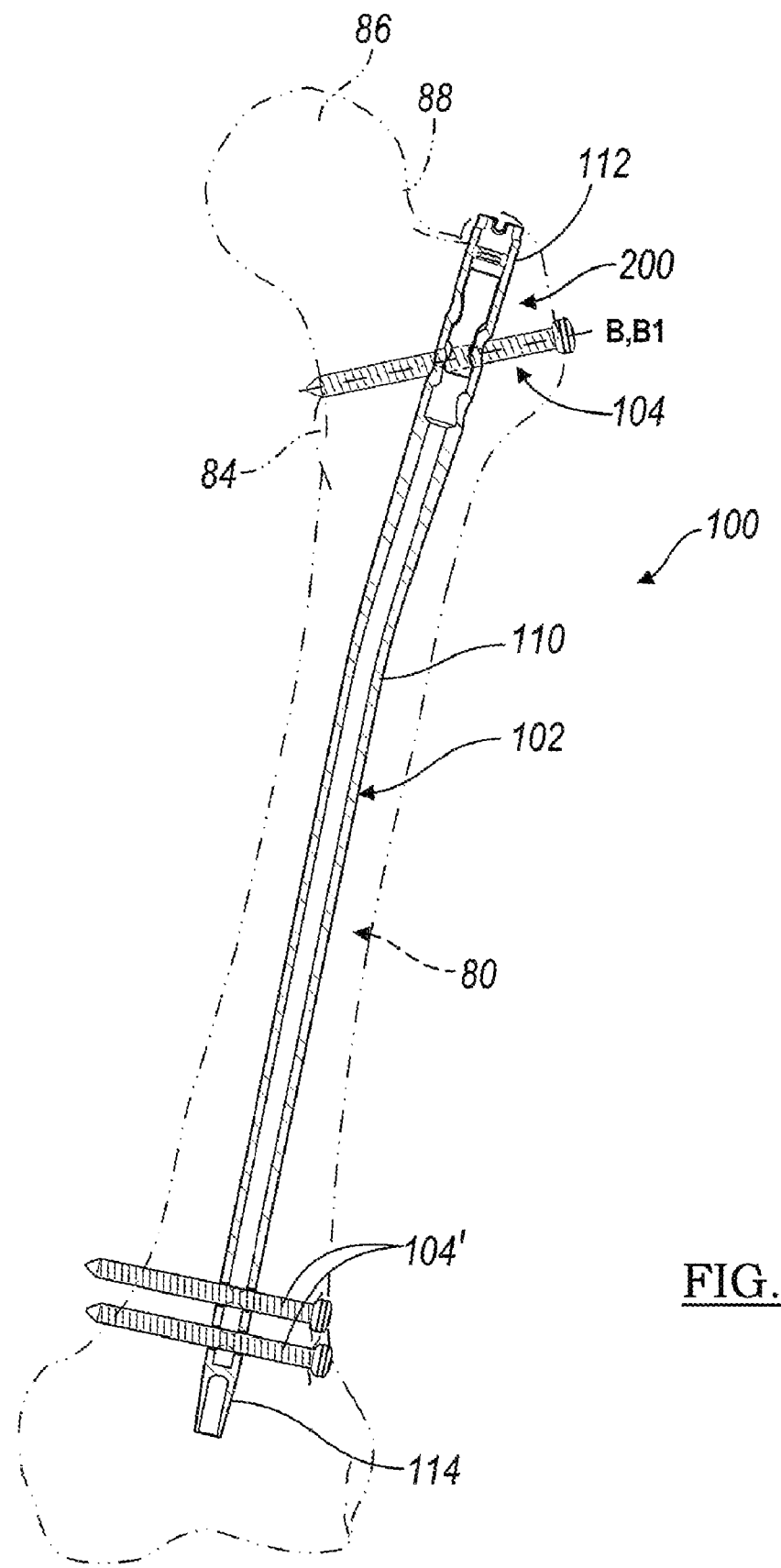
FIG. 1 is an environmental view of a fixation device according to the present teachings, illustrating a trochanteric procedure with interlocking fixation fasteners.

The following description is merely exemplary in nature and is in no way intended to limit the invention, its application, or uses. For example, although the present teachings are illustrated for exemplary trochanteric, piriformis and retrograde procedures with reconstructive or interlocking femoral fixation, and for proximal tibial fixation, the present teachings can be used for other fixation procedures involving long bones. It will be understood that general surgical procedures are outlined only as needed to illustrate the devices and methods provided by the present teachings, while detailed descriptions of standard and known procedures and instruments are omitted for simplicity.

Exemplary fixation devices 100 are illustrated and described below. FIGS. 1-6C illustrate fixation devices for trochanteric femoral fixation, FIGS. 7-9B for retrograde femoral fixation, FIGS. 10-14C for piriformis femoral fixation, and FIGS. 15-19B for cortical tibia fixation. Although some of the structural details and/or sizes of the fixation components for each procedure may differ, each fixation device 100 can include an intramedullary nail or implant 102, a telescopic clamp or securing device 200 that includes a hollow insert or similar movable member 160 and a cannulated set screw or similar locking member 180, and various bone fasteners, including single-piece interlocking fasteners 104 and reconstruction fasteners 140, including lag screws and telescopic screws slidable within sleeves. The movable member 160 can be cannulated and can include a plurality of openings defining guiding bores configured for guiding the orientation of corresponding bone fasteners, as is described below in reference to particular procedures. In the interest of brevity, details described with respect to one procedure will generally not be repeated in other procedures. For example, although dynamic and static engagement positions of the movable member 160 of the telescopic clamp/securing device 200 device are illustrated with respect to tibial procedures in FIGS. 18A and 18B, it will be understood that telescopic clamp/securing device 200 device can operate similarly in all the other procedures.

Figure 1A:
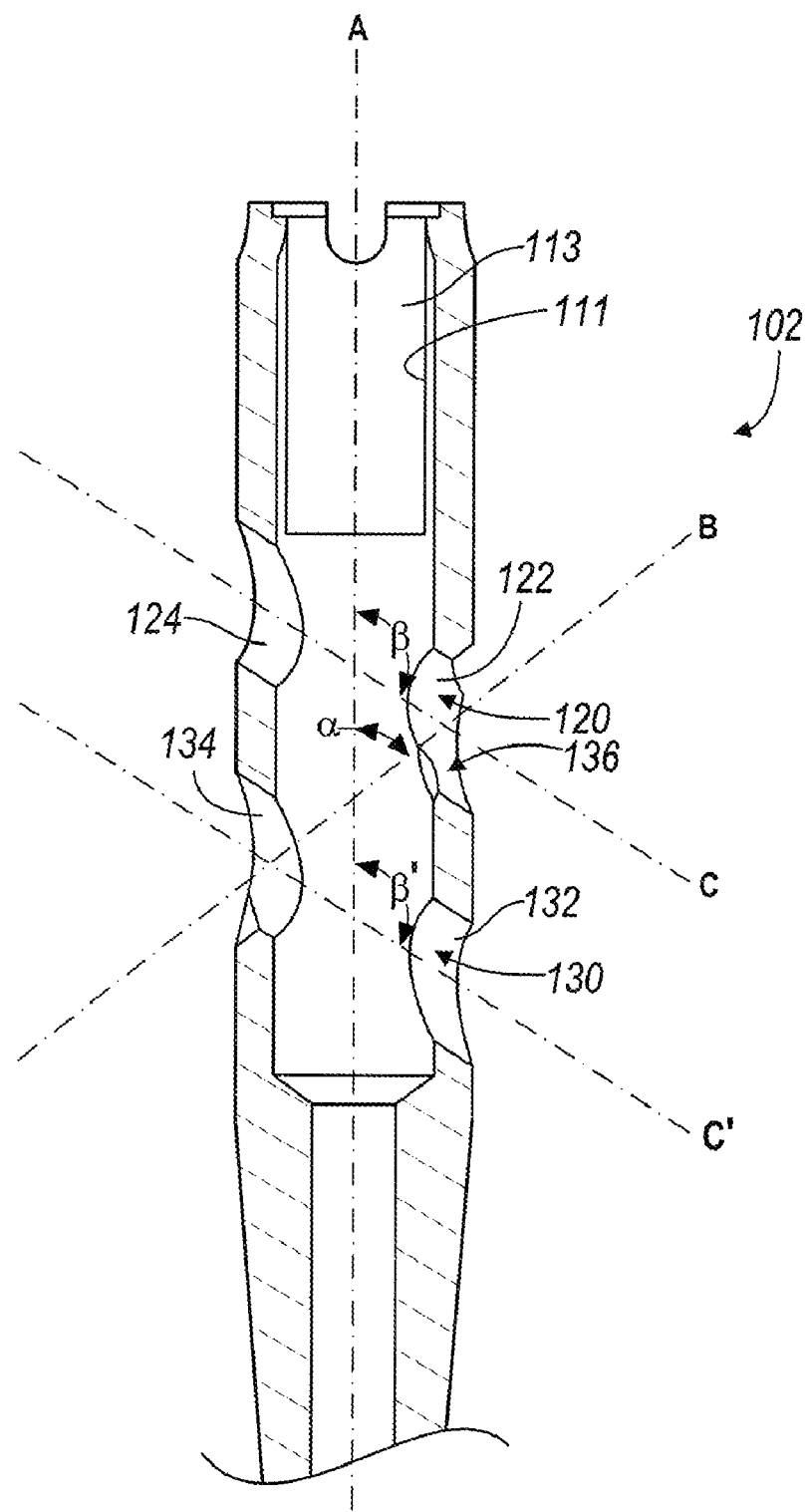
FIG. 1A is a sectional view of a proximal portion of an intramedullary implant of the fixation device of FIG. 1.
Figure 2:
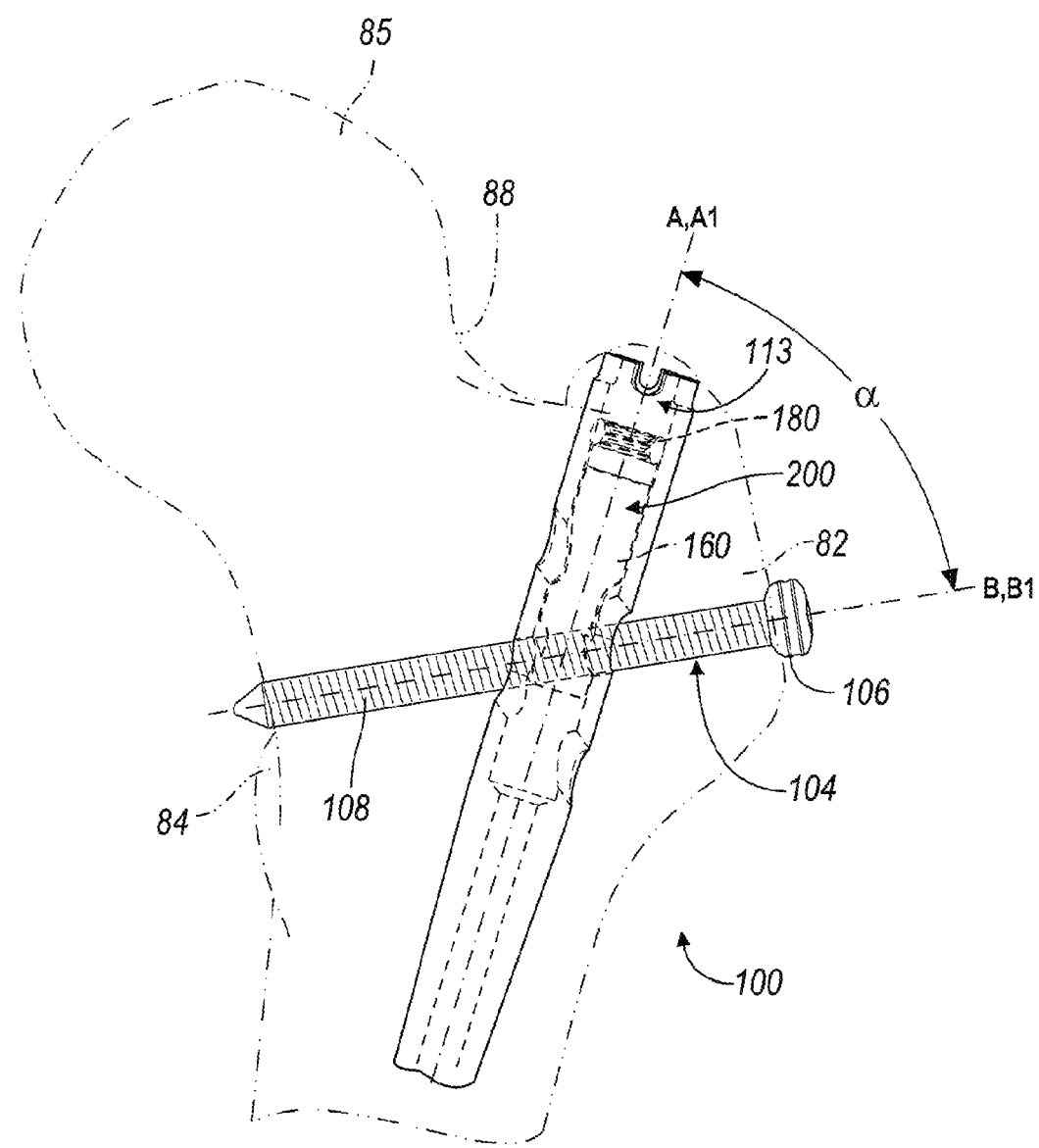
FIG. 2 is an enlarged view of a detail of FIG. 1.

Referring to FIGS. 1, 1A, and 2, an exemplary fixation device 100 according to the present teachings is shown implanted in a femur 80 for an interlocking trochanteric procedure. The fixation device 100 can include an elongated intramedullary implant 102 and an elongated interlocking fastener 104. The intramedullary implant 102 can include a shaft 110 having proximal and distal portions 112, 114 and received in the intramedullary canal of the femur 80. The proximal portion 112 of the intramedullary implant 102 can include a proximal longitudinal bore 113 defining a longitudinal axis A. A proximal inner surface 111 of the proximal longitudinal bore 113 can be of elliptical or other non-circular shape, having different major and minor diameters such that the cross-section has an elongated shape.

The proximal portion 112 of the intramedullary implant 102 can include first and second fastener bores 120, 130 along first and second axes C and C' at first and second angles β and β' relative to the longitudinal axis A, as shown in FIG. 1A. The axes C and C' can be parallel such that the angles β and β' are substantially equal. The first bore 120 can be defined by first and second opposite-side openings 122 and 124 that can be offset along the direction of axis A, thereby defining the first axis C at an angle β relative to the axis A. The second bore 130 can be defined by third and fourth opposite-side openings 132 and 134 that can be offset along the direction of axis A, such that they define the second axis C' at an angle β' relative to the axis A. The first, second, third and fourth opening 122, 124, 132, 134 can have closed perimeters. The first and fourth openings 122, 134 can define a third fastener bore 136 along an axis B at an angle α relative to the longitudinal axis A, as shown in FIG. 1A.

The interlocking fastener 104 can be oriented along the axis B passing through fastener bore 136 of the intramedullary implant 102. The interlocking fastener 104 can extend from a proximal lateral position near the greater trochanter 82 to a more distal medial position near the lesser trochanter 84 of the femur 80, as shown in FIG. 2. The interlocking fastener 104 can include a head 106 and a shaft 108 with threads, ridges or other anchoring formations. One or more fasteners 104', generally similar in structure to the interlocking fastener 104, can be inserted through the distal portion 114 of the intramedullary implant 102 for fixation to the distal femur.

Figure 3:
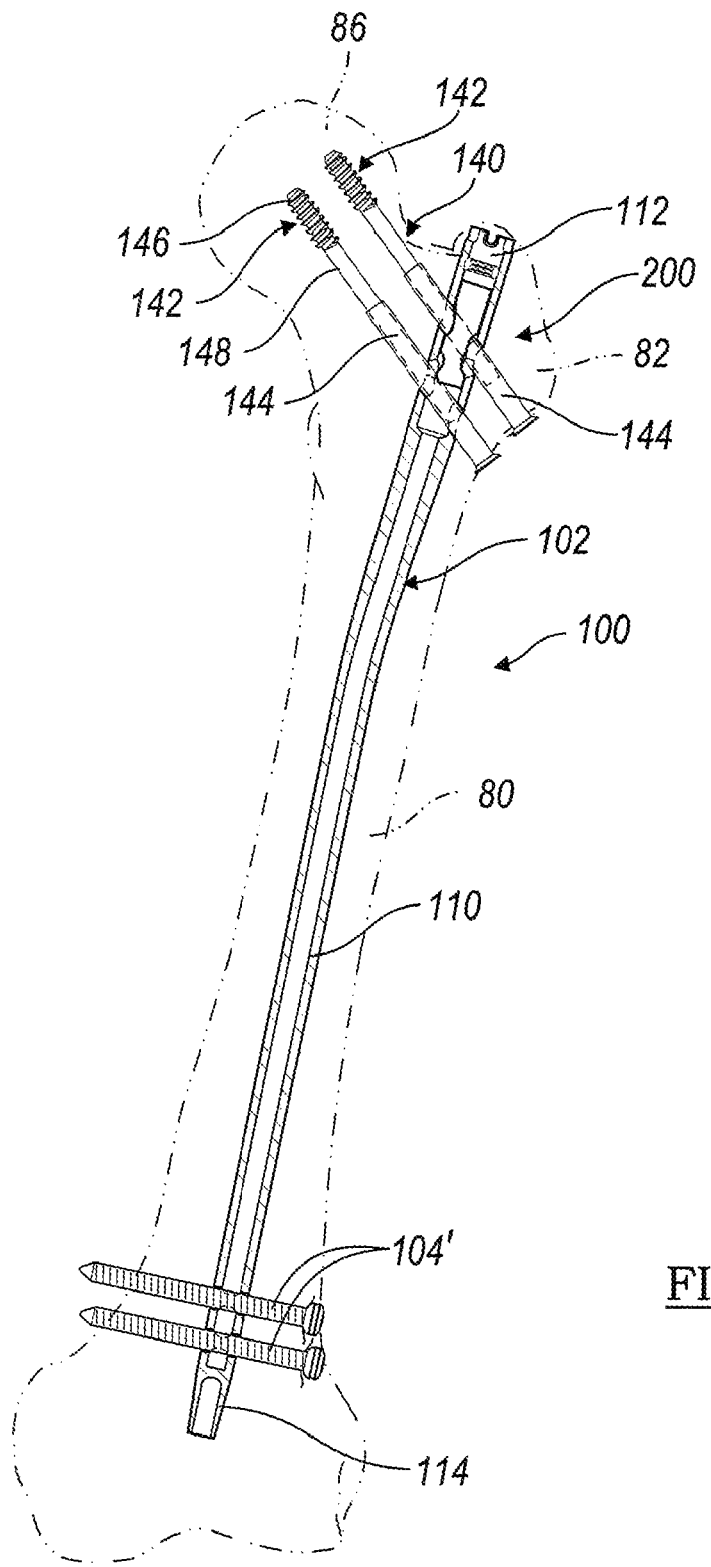
FIG. 3 is an environmental view of a fixation device according to the present teachings, illustrating a trochanteric procedure with reconstruction fixation fasteners.
Figure 4:
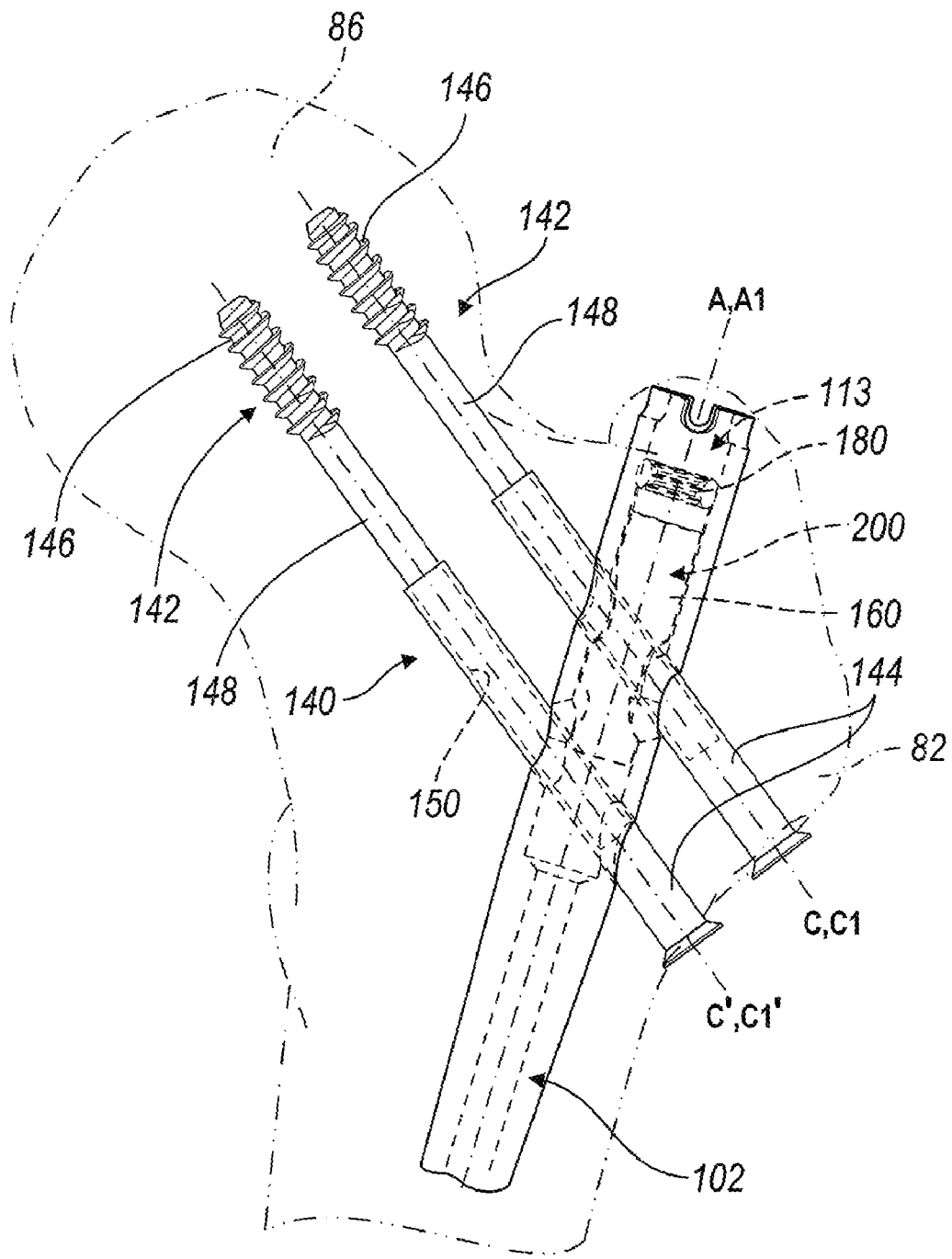
FIG. 4 is an enlarged view of a detail of the fixation device of FIG. 3.
Figure 4A:
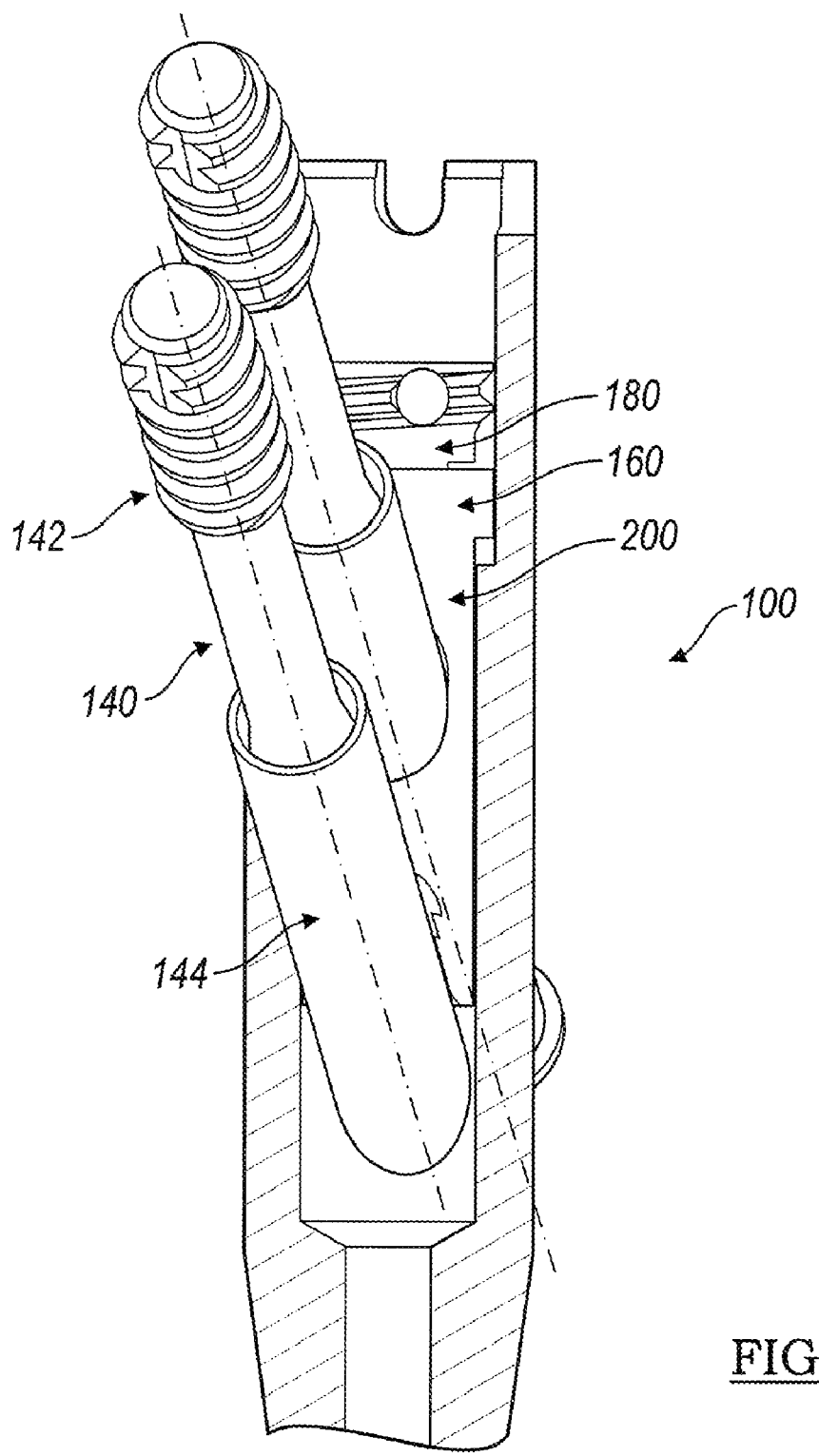
FIG. 4A is a partial cut-out view of a detail of the fixation device of FIG. 3

Referring to FIGS. 1A, 3 and 4, another exemplary fixation device 100 according to the present teachings is shown implanted in the femur 80 for a reconstructive trochanteric procedure. Two reconstruction fasteners 140 can be oriented along the directions defined by the first and second axes C and C' passing through the corresponding first and second fastener bores 120, 130 of the intramedullary implant 102. Accordingly, the reconstruction fasteners 140 can be oriented at respective first and second angles β and β' relative to the longitudinal axis A, as described above. The reconstruction fasteners 140 can extend from the vicinity of the greater trochanter 82 through the femoral neck 88 and into the femoral head 86. Each reconstruction fastener 140 can be a two-piece telescoping component including a sleeve 144 having a longitudinal bore 150 and a lag screw 142 that can pass through the bore 150 of the sleeve 144 and can slide relative to the sleeve 142. The lag screw 142 can include an unthreaded portion 140 receivable in the bore 150 of the sleeve 144, and a threaded or bone anchoring portion 146.

Referring to FIGS. 1-6C, either the interlocking fastener 104 or the reconstruction fasteners 140 can be secured to the intramedullary implant 102 using a securing device 200. The securing device 200 can include a telescopic insert or movable member 160, and a locking member 180, such as a set screw. The movable member 160 can be adapted for locking multiple fasteners to the intramedullary implant 102, as shown in FIGS. 2 and 4. The movable member 160 can include a circular longitudinal bore 162 defining longitudinal axis "A1". When the movable member 160 is inserted into the longitudinal bore 113 of the intramedullary implant 102, the longitudinal axes A and A1 can substantially coincide. The movable member 160 can define first and second guiding bores 164, 166 oriented along the first and second axes C1, C1', as shown in FIG. 5C. When the movable member 160 is inserted into the bore 113 of the intramedullary implant 102, the first and second axes C, C' of the intramedullary implant can substantially coincide with the first and second axes C1, C1' of the movable insert 160.

Figure 5A:
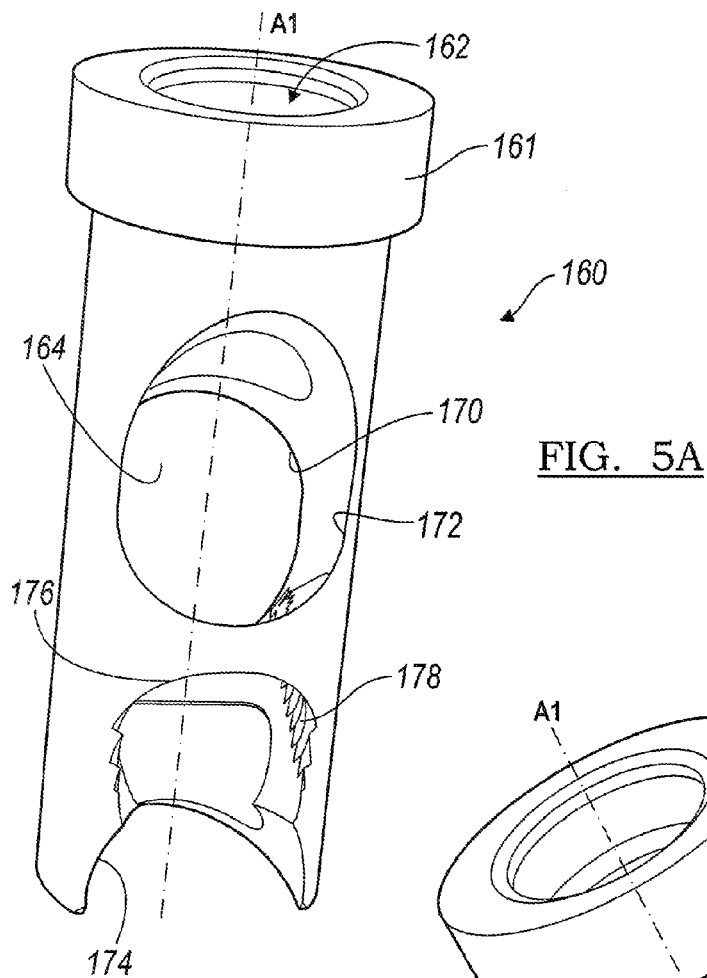
FIG. 5A-C are various perspective view of an insert for the fixation devices of FIGS. 2 and 3.
Figure 5B:
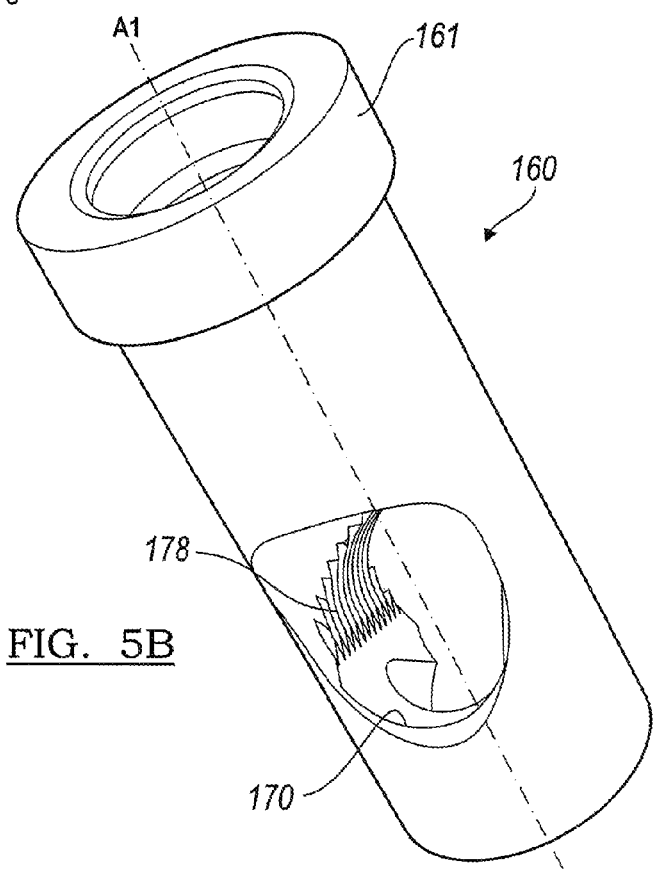
Figure 5C:
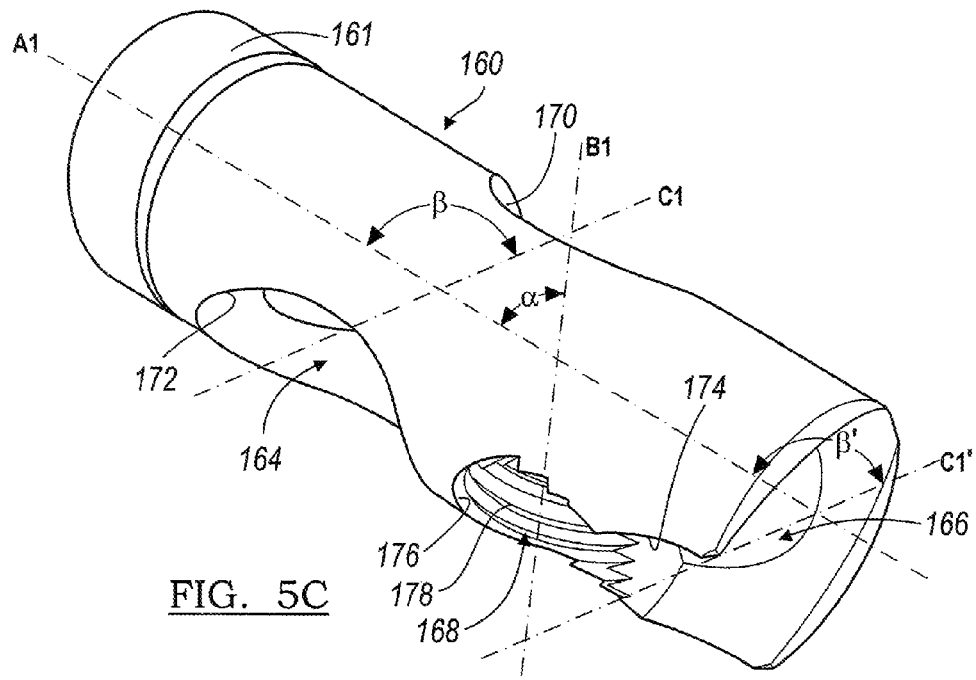

The first guiding bore 162 can be fully enclosed within the movable member 160 and defined by first and second openings 170, 172. The first and second opening 170, 172 can be axially offset, can have closed perimeters and can be formed on opposing sides of the movable insert 160 along the first axis C1. The second guiding bore 166 can be partially enclosed and defined by a third opening 174 having an open perimeter, as shown in FIG. 5C. It will be appreciated, however, that the second guiding bore 166 can also be fully enclosed and defined by two opposing openings along the axis C1' of the movable member 160. The first and second reconstruction fasteners 140 can be inserted through the first and second guiding bores 164, 166 of the movable member 160 and through the corresponding first and second fastener bores 120, 130 of the intramedullary implant 102 along the axes C, C', as shown in FIG. 4.

The movable member 160 can also include a third guiding bore 168 defined along axis B1 and at an angle α relative to the longitudinal axis A1. When the movable member 160 is inserted into the longitudinal bore 113 of the intramedullary implant 102, the axes B and B1 can substantially coincide. The guiding bore 168 can be defined by the first opening 170 and an opposite-side and longitudinally offset and open-perimeter fourth opening 176. The perimeter of the opening fourth 176 can intersect the perimeter of the third opening 174, such that the fourth and third openings 174, 176 can communicate, as shown in FIGS. 5A and 5C. An interlocking fastener 104 can be received in the third guiding bore 168 passing through the third fastener bore 136 of the intramedullary implant 102, when reconstruction fasteners 140 are not used, as shown in FIG. 2. Ridges or other engagement formations 178 can be provided in portions of any guiding bores of the movable member 160 for engaging corresponding threads or ridges 108 of interlocking fasteners 104. Ridges 178 are illustrated, for example, in FIGS. 5A-5C in connection with trochanteric femoral procedures, in FIGS. 9A-9C for retrograde femoral procedures, in FIGS. 14A and 14B for piriformis femoral procedures, and in FIGS. 16, 17B, 18A and 18C for tibial procedures. The ridges 178 allow removal or backing out of an individual interlocking fastener 104 by rotating the head 106 of interlocking fastener 104 in a counterclockwise direction with a driver, for example, while the intramedullary implant 102 and the other interlocking fasteners 104 remain secured in place with the securing device 200 in a locked position. Accordingly, any interlocking fastener 104 can be removed or backed out without accessing the top of the intramedullary implant 102 for disengaging the interlocking fastener 104. Therefore, the procedure described below in connection with FIGS. 19A and 19B for unlocking the securing device 20 need not be used for backing out or completely removing one of the interlocking fasteners 104.

Figure 5D:
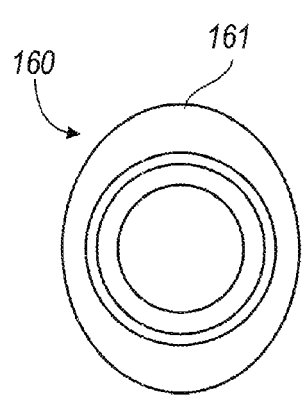
FIG. 5D is a top view of the insert if FIG. 5A.
Figure 5E:
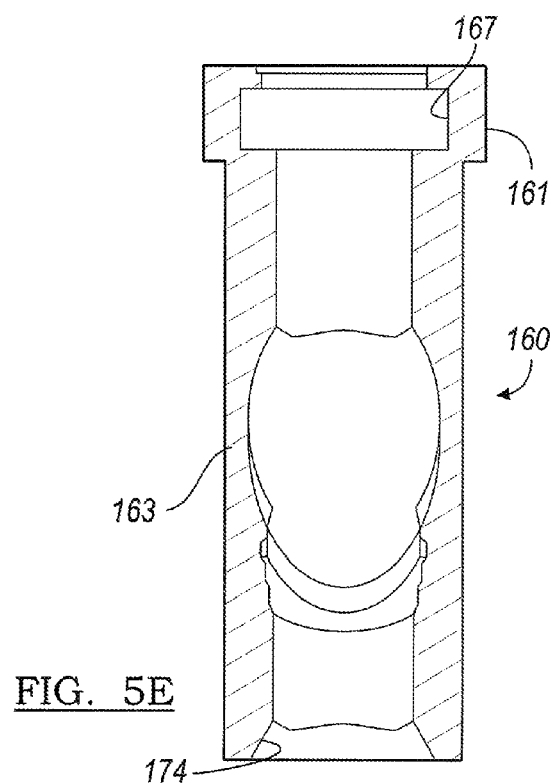
FIG. 5E is a sectional view of the insert of FIG. 5A.
Figure 15:
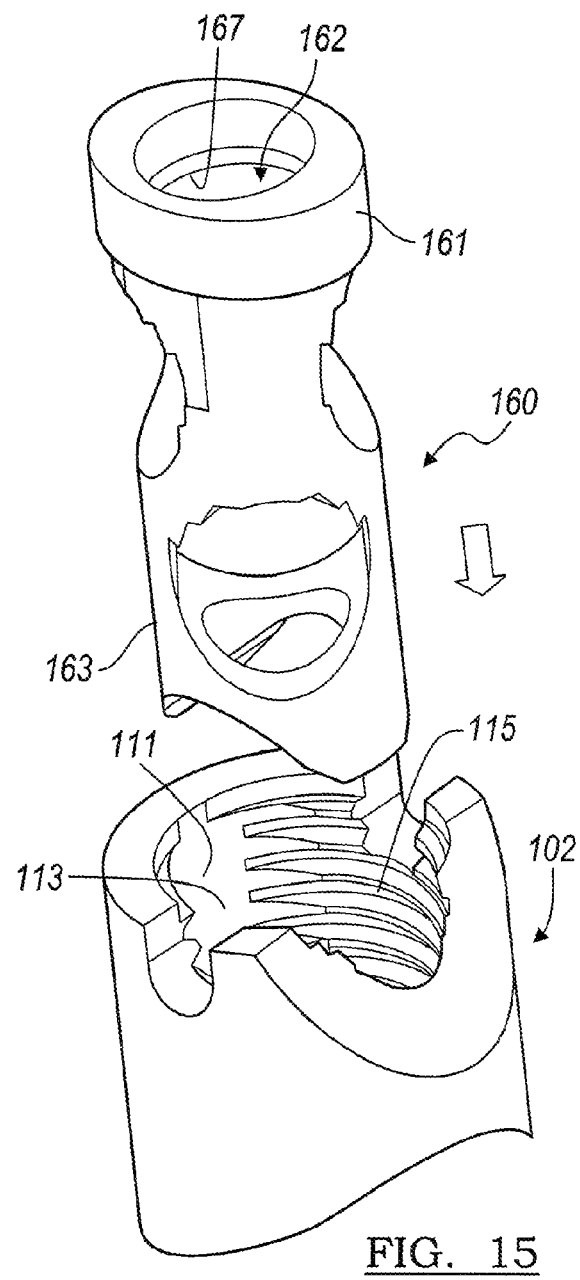
FIG. 15 is a partially exploded perspective view of a portion of a fixation device according to the present teachings.

Referring to FIGS. 5D and 5E, the movable member 160 can include a proximal end portion having an outer surface 161 with elliptical or elongated cross-section, and a body with a circular cylindrical surface 163, as shown in FIGS. 5D and 5E. The outer surface 161 of the movable member 160 can mate with the inner surface 111 of the proximal longitudinal bore 113 providing a keyed insertion, such that the movable member 160 can be inserted in the proximal longitudinal bore 113 in either one of two directions that are 180 degrees apart, as illustrated in FIG. 15 in connection with a movable member 160 and an intramedullary implant 102 for a tibial procedure described below. The longitudinal inner bore 162 of the movable member 160 can be circular.

Figure 6A:
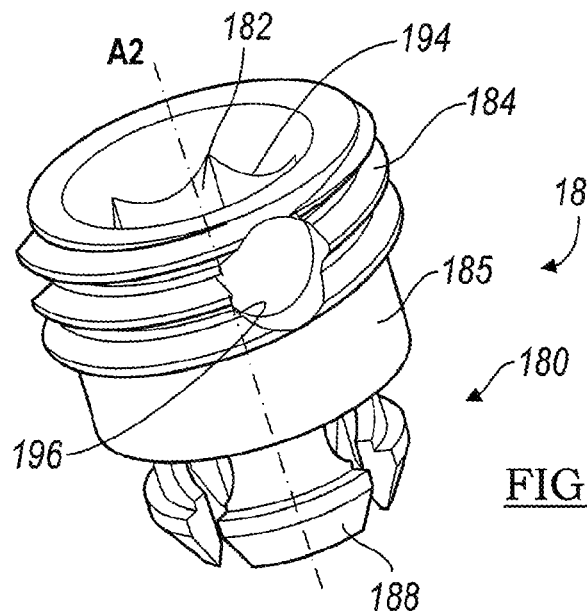
FIG. 6A is a perspective view of a locking member according to the present teachings.
Figure 6B:
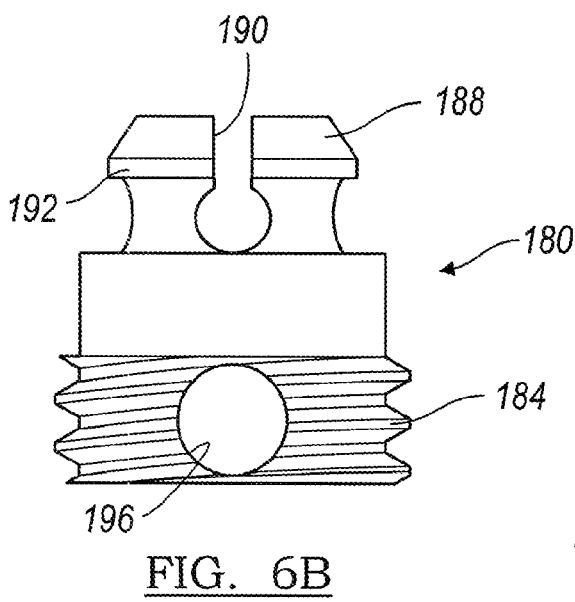
FIG. 6B is a side view of the locking member of FIG. 6A.
Figure 6C:
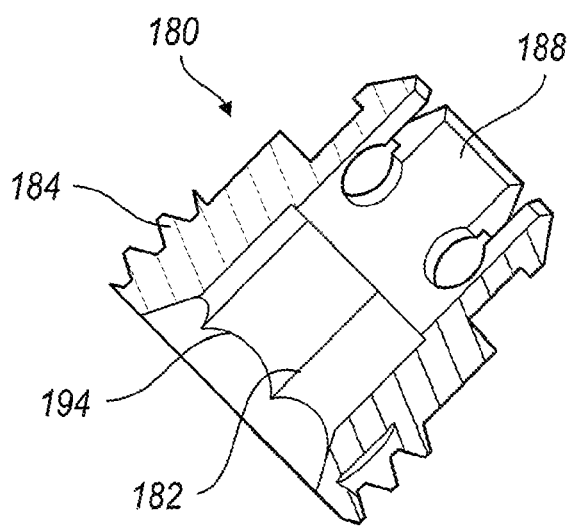
FIG. 6C is a sectional view of the locking member of FIG. 6A.
Figure 7:
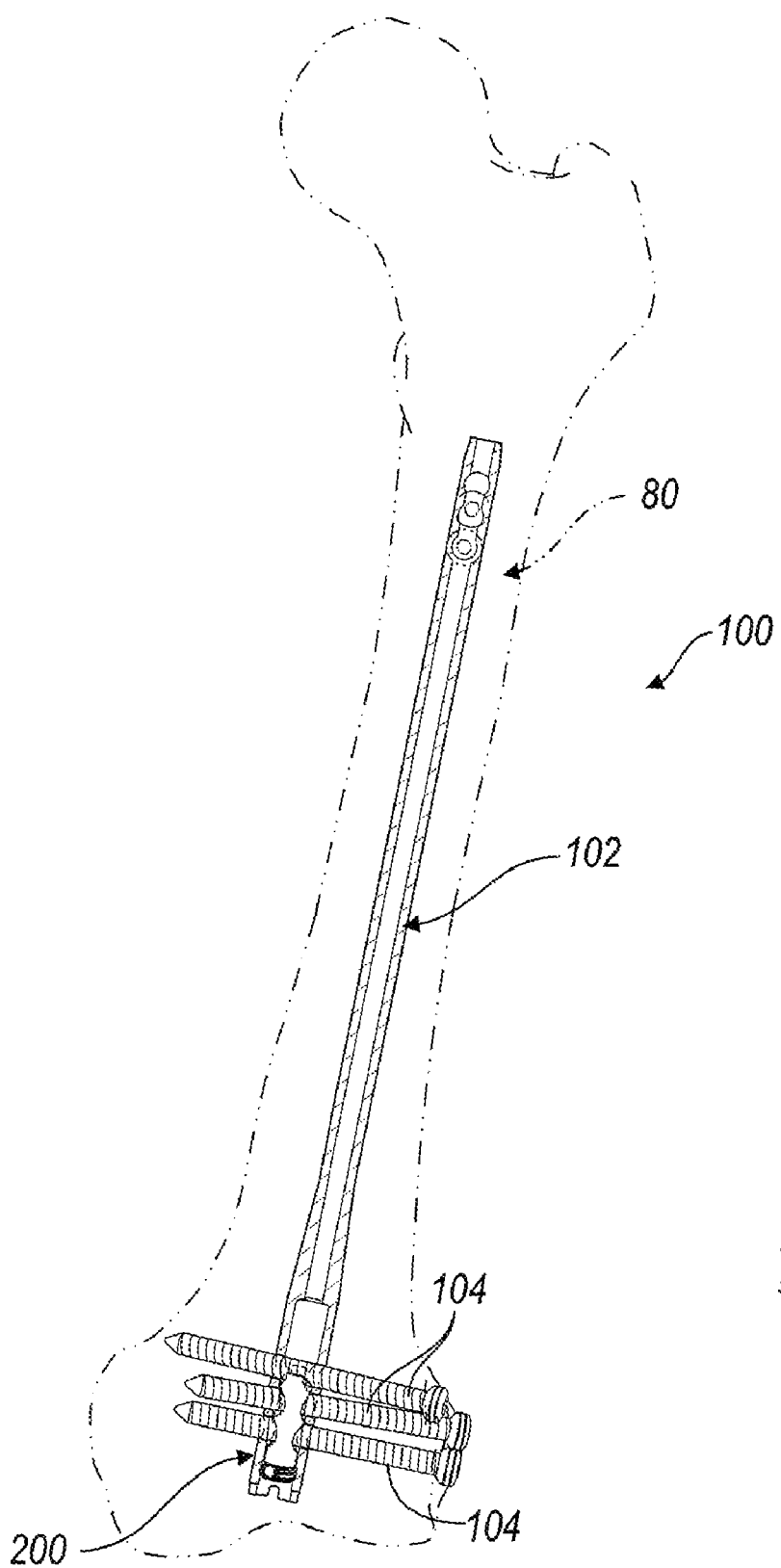
FIG. 7 is an environmental view of a fixation device according to the present teachings, illustrating a retrograde femoral procedure.
Figure 16:
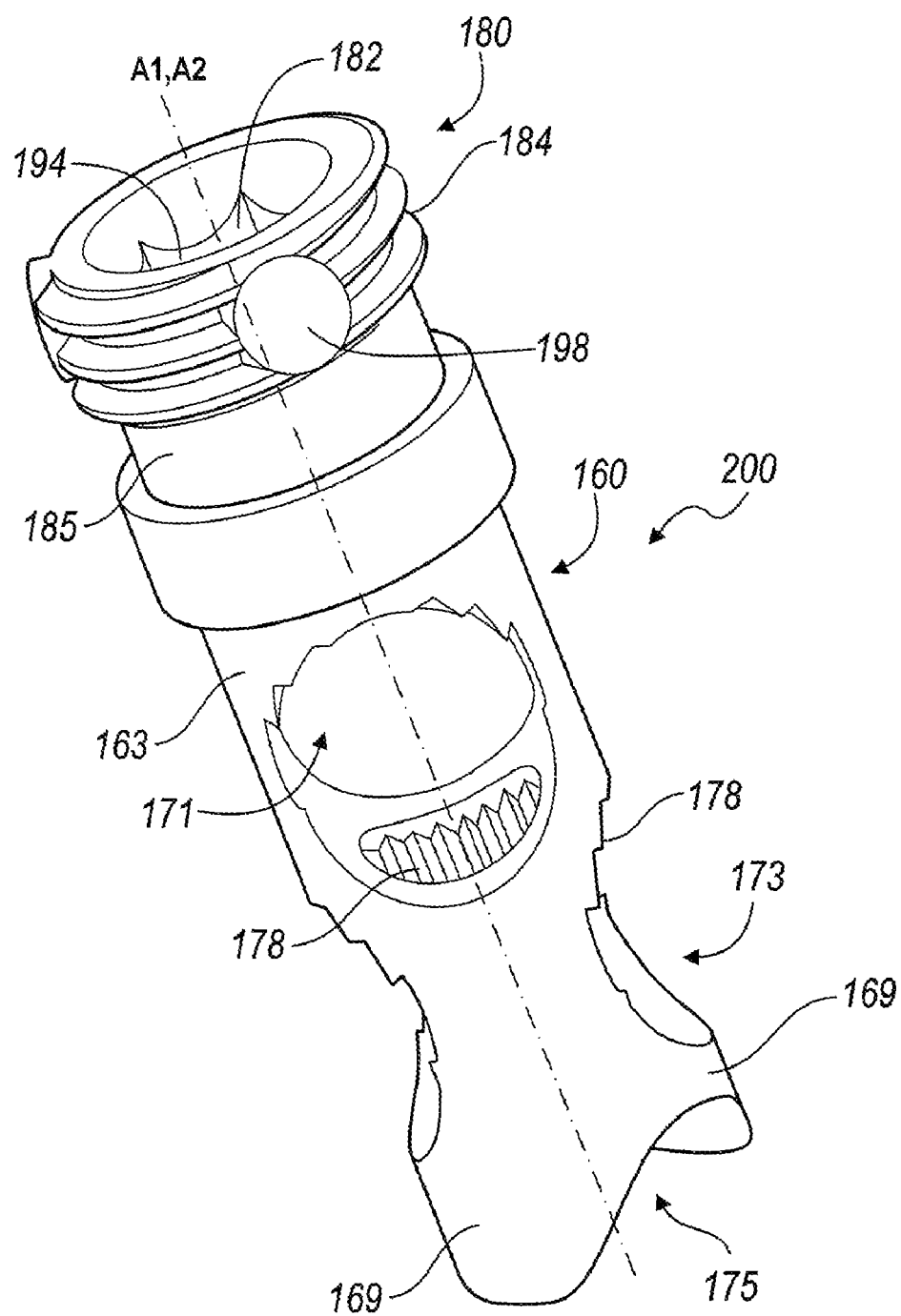
FIG. 16 is a perspective view illustrating an insert assembled with a locking member for an intramedullary nail according to the present teachings.

Referring to FIGS. 6A-6C, various views of a locking member 180 are illustrated. The locking member 180 can include a longitudinal bore 182 along a longitudinal axis A2. The locking member 180 can include a threaded portion 184 and an unthreaded cylindrical portion 185. The threaded portion 184 can threadably engage a threaded inner surface 115 of the proximal longitudinal bore 113 of the intramedullary implant 102, as shown in FIGS. 15 and 16 in connection with a movable member 160 and intramedullary implant 102 for a tibial procedure described below. The locking member 180 can also include a distal flexible or resilient portion 186 defined by a plurality of legs 188 extending from the unthreaded portion 185 of the locking member 180 and separated by slots 190. The resilient portion 186 can define a step or flange 192 that can be retained into a groove 167 of the movable member 160, shown in FIG. 5E, for example, when the resilient portion 186 is snap-fitted into the longitudinal bore 162 of the movable member 160, as shown in FIGS. 15 and 16.

The locking member 180 can also include a driver engagement formation 194 in a proximal portion of the bore 182 for engaging a driver 500. The driver 500 can be rotated for threadably engaging the locking member 180 with the intramedullary implant 102, such that advancement of locking member 180 and corresponding advancement of the movable member distally or proximally can engage or disengage the movable member 160 from corresponding bone fasteners, such as fasteners 104, as shown in FIGS. 19A, 19B, 18A and 18B, in connection with a tibial procedure, as described in further detail below. The locking member 180 can also include holes or other openings 196 that interrupt the threads of the threaded portion 184. The openings 196 can be plugged with thread locks 198 that prevent further engaging or disengaging movement between the locking member 180 and the intramedullary implant 102, thereby securing the corresponding position of the movable member 160 relative to the intramedullary implant 102 and the fasteners 104 or 140. The thread locks 198 can be made of polyethylene, for example.

Figure 8:
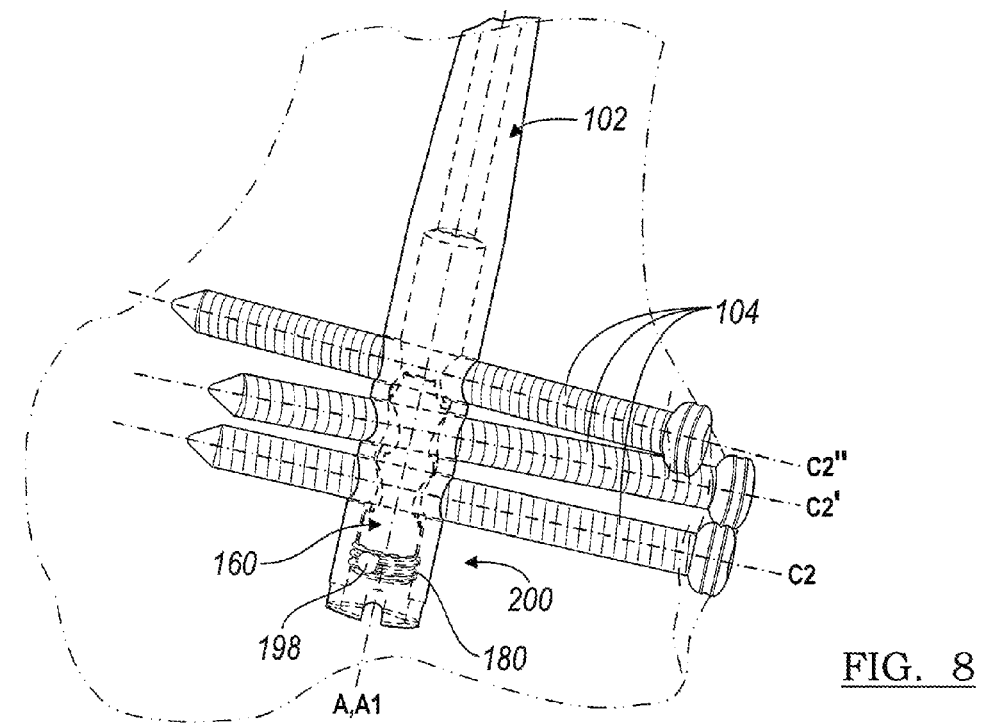
FIG. 8 is an enlarged view of a detail of FIG. 7.
Figure 8A:
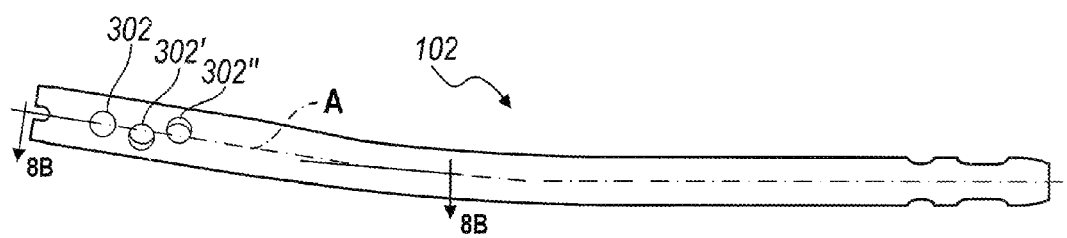
FIG. 8A is a side view of an intramedullary implant of the fixation device of FIG. 7.
Figure 8B:
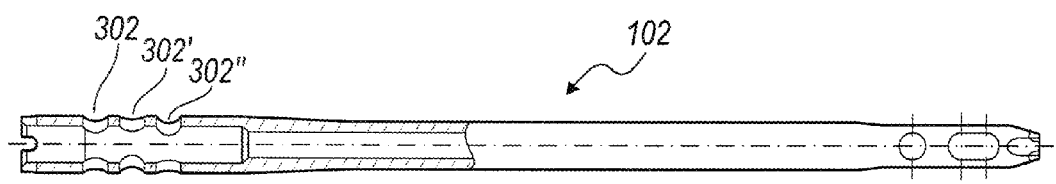
FIG. 8B is another side view of an intramedullary implant of the fixation device of FIG. 7, shown partially in section.
Figures 9A, 9B:
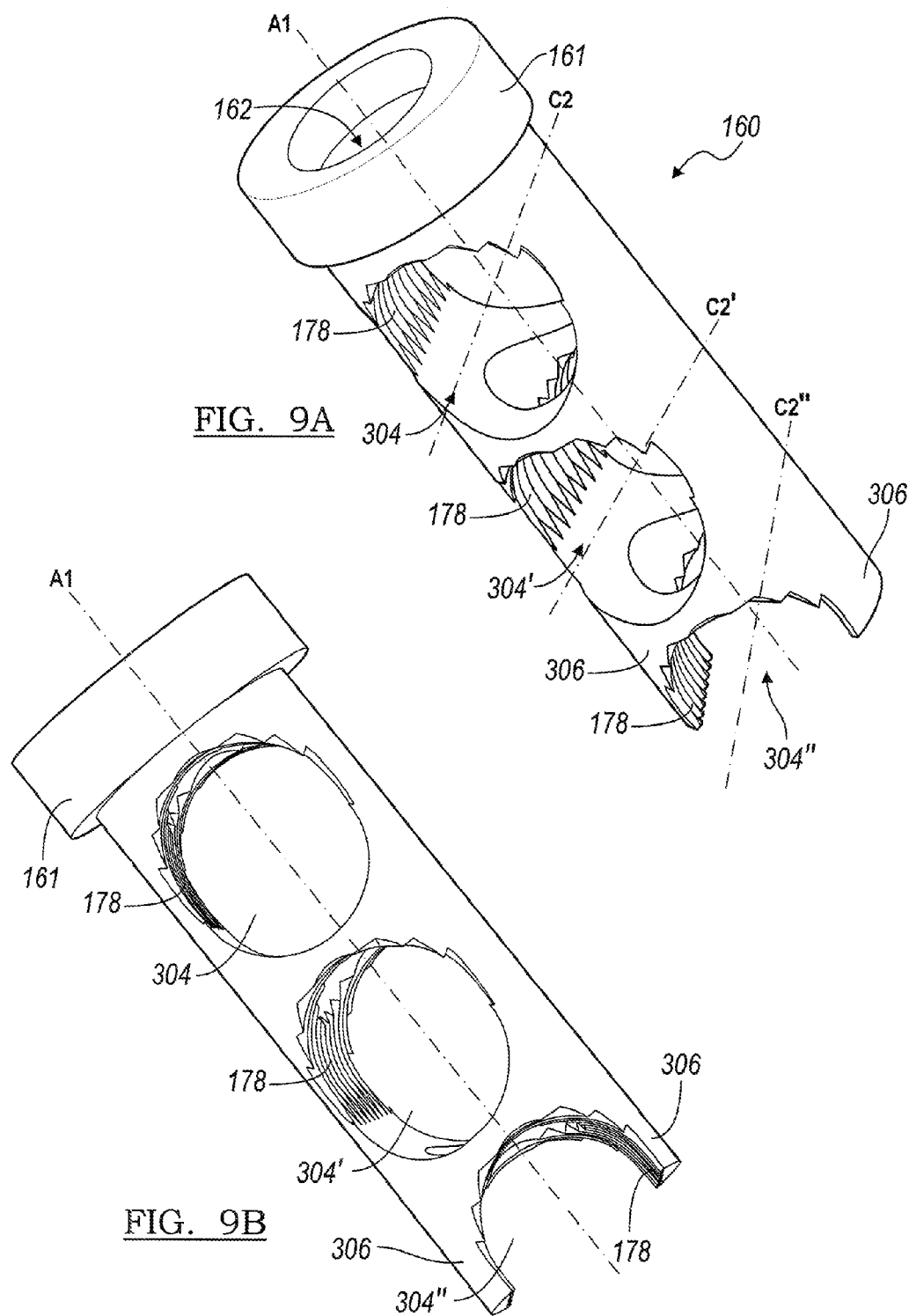
FIGS. 9A and 9B are perspective views of an insert for the fixation device of FIG. 7.
Figure 9C:
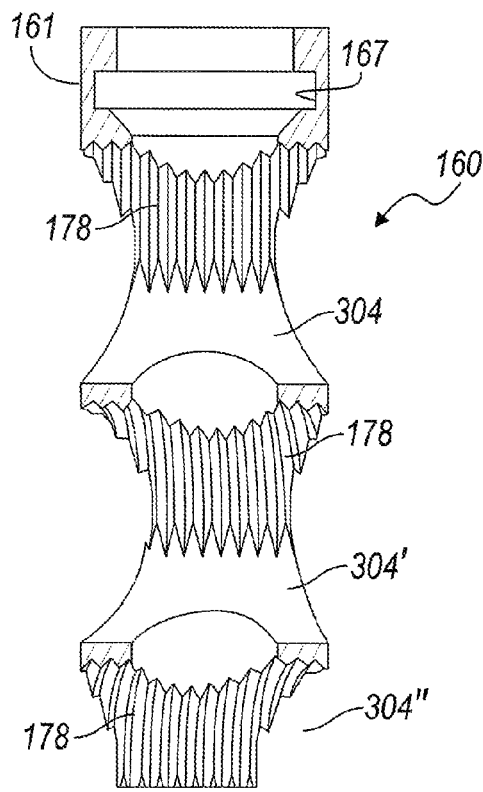
FIG. 9C is a sectional view of the insert of FIG. 9A.

Referring to FIGS. 7-9B, an exemplary fixation device 100 is illustrated for a retrograde interlocking femoral fixation procedure. The retrograde intramedullary implant 102 can be inserted in the distal portion of the femur 80 in a retrograde direction and can interlock at least up to three bone fasteners 104 using the movable member 160 and the locking member 180 of the securing device 200. The retrograde intramedullary implant 102 can define a plurality of through-bores, for example first, second and third bores 302, 302', 302" oriented transversely or at other different angles relative to longitudinal axis A of the retrograde intramedullary implant 102. Some of the bores 302, 302', 302" can circumferentially offset relative to the longitudinal axis A, or can be aligned along the longitudinal axis A, as shown in FIG. 8A. The movable member 160 can include corresponding first, second and third guiding bores 304, 304', 304" oriented along first, second and third axes C2, C2', and C2', as shown in FIGS. 8 and 9A. The first and second guiding bores 304, 304' can have closed perimeters, while the third guiding bore 304" can have an open perimeter defining a pair of opposing legs 306. Some of the first, second and third guiding bores 304, 304', 304'" can be aligned or circumferentially offset relative to one another or relative to the longitudinal axis A1, and can be parallel or non-parallel. The structure and function of the locking member 180 and other features of the securing device 200 and retrograde intramedullary implant 102 are similar to those described above in connection with trochanteric procedure illustrated in FIGS. 1-6C and are not repeated.

Figure 10:
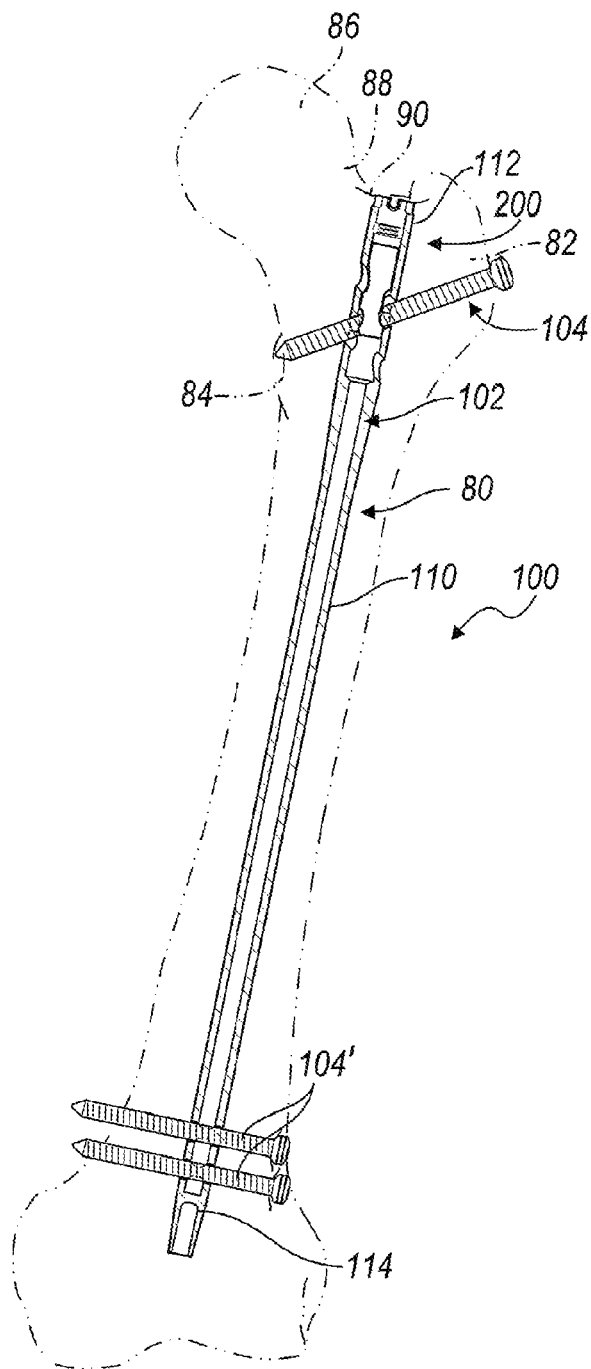
FIG. 10 is an environmental view of a fixation device according to the present teachings, illustrating a piriformis procedure with interlocking fixation fasteners.
Figure 11:
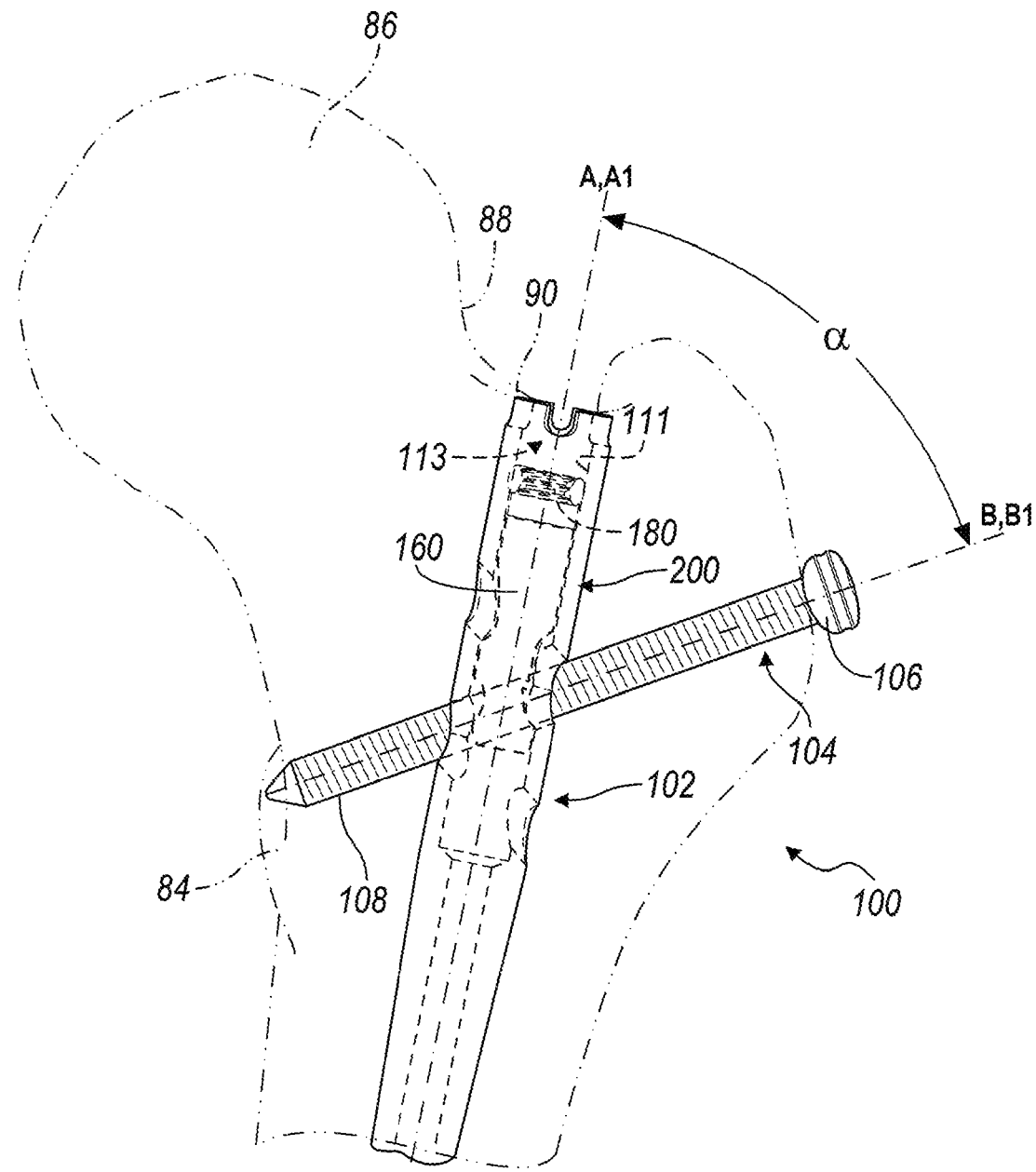
FIG. 11 is an enlarged view of a detail of FIG. 10.
Figure 12:
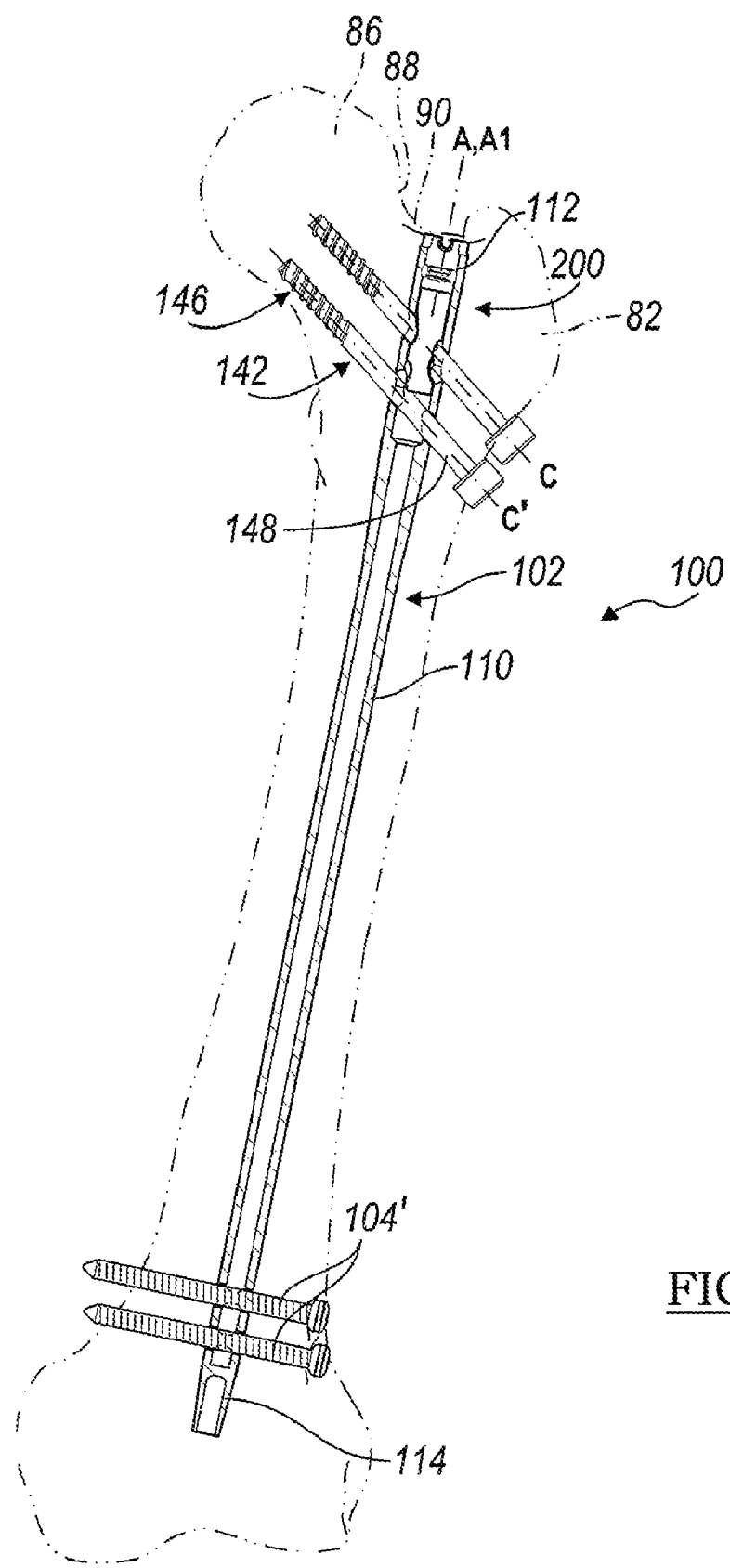
FIG. 12 is an environmental view of a fixation device according to the present teachings, illustrating a piriformis procedure with reconstruction fixation fasteners.
Figure 13:
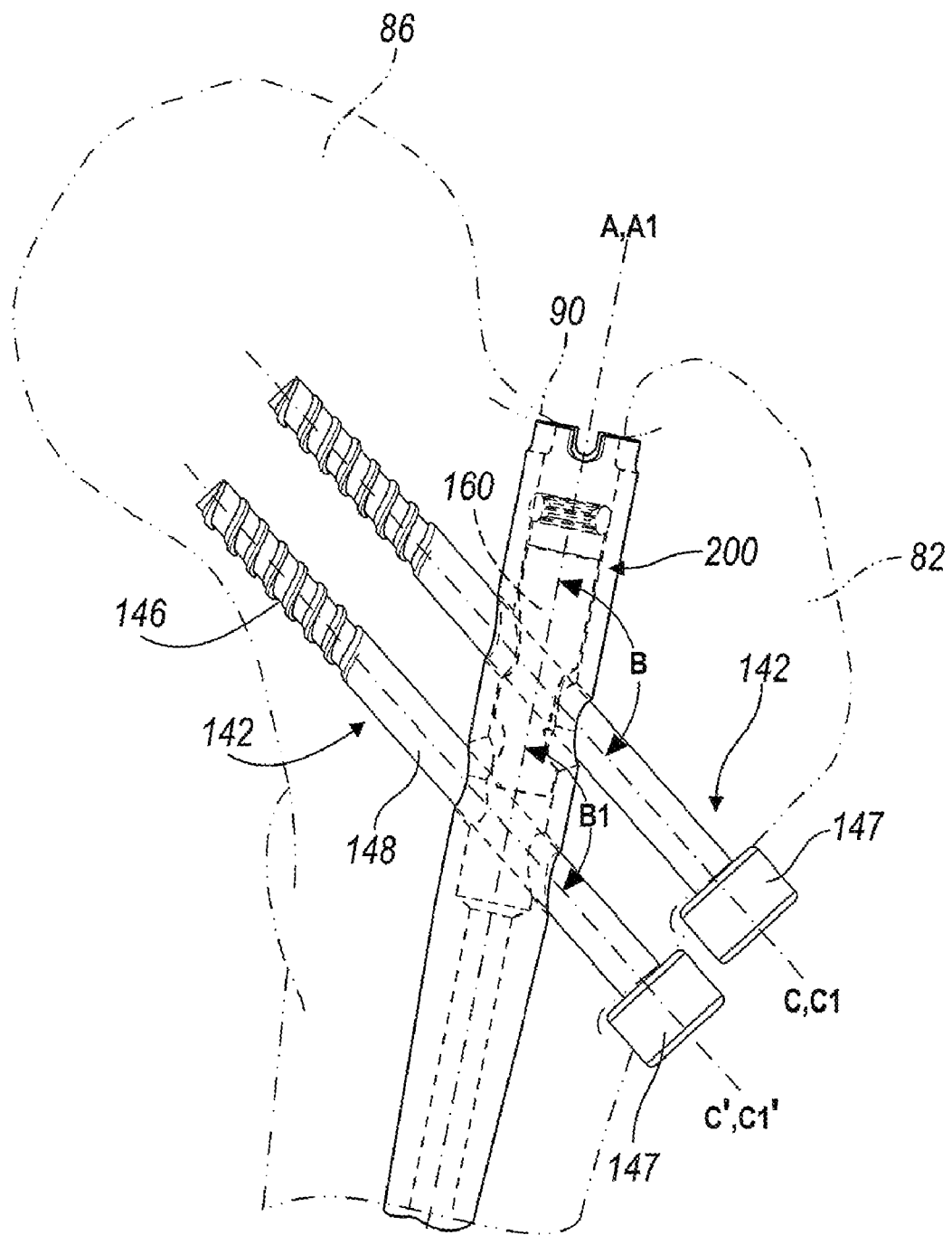
FIG. 13 is an enlarged view of a detail of FIG. 12.
Figure 14C:
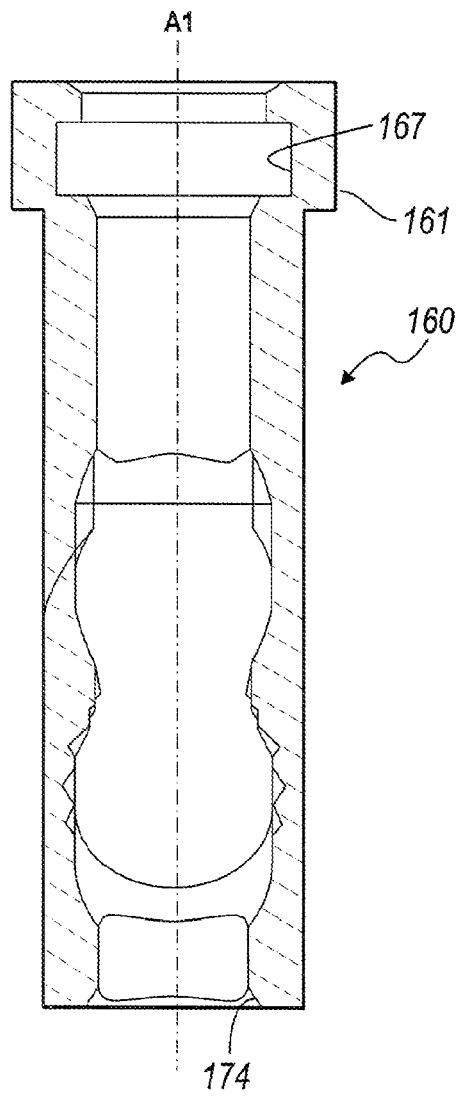
FIG. 14C is a sectional view of the insert of FIG. 14A.

Referring to FIGS. 10-14B, an exemplary fixation device 100 according to the present teachings is illustrated for piriformis femoral procedures. FIGS. 10 and 11 illustrate an interlocking piriformis fixation procedure, and FIGS. 12 and 13 illustrate a reconstruction piriformis fixation procedure. The piriformis intramedullary implant 102, the piriformis interlocking fastener 104 and the piriformis securing device 200 are similar to the corresponding components described in connection with the trochanteric procedures illustrated in FIGS. 1-6C and their description is not repeated, except to note different or additional elements. The piriformis intramedullary implant 102 can be configured for entry through the piriformis fossa near the greater trochanter 82, as shown in FIG. 11. The reconstruction fasteners 140 can include single-piece piriformis lag screws 142 having a threaded portion 146, an unthreaded portion 148 and a head 147, as shown in FIG. 13. The piriformis lag screws 142 can pass through the piriformis intramedullary implant 102 along axes C, C', and through the piriformis movable member 160 of piriformis securing device 200 along corresponding axes C1, C1' at angles β and β', which can be equal or different. The piriformis lag screws 142 can be also be used with sleeves 144 in a telescopic manner, as described in connection with the trochanteric procedure illustrated in FIG. 4. Various views of the piriformis movable member 160 are illustrated in FIGS. 14A-14C using the same reference characters as used in FIGS. 5A-5E to describe similar elements.

Figure 17A:
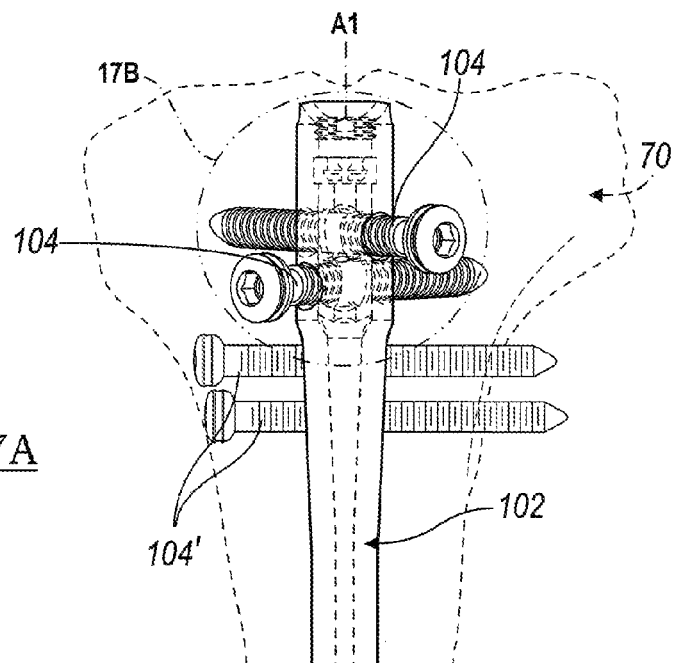
FIG. 17A is an environmental perspective view of a fixation device according to the present teachings, illustrating a femoral procedure with transverse fixation fasteners.
Figure 17B:
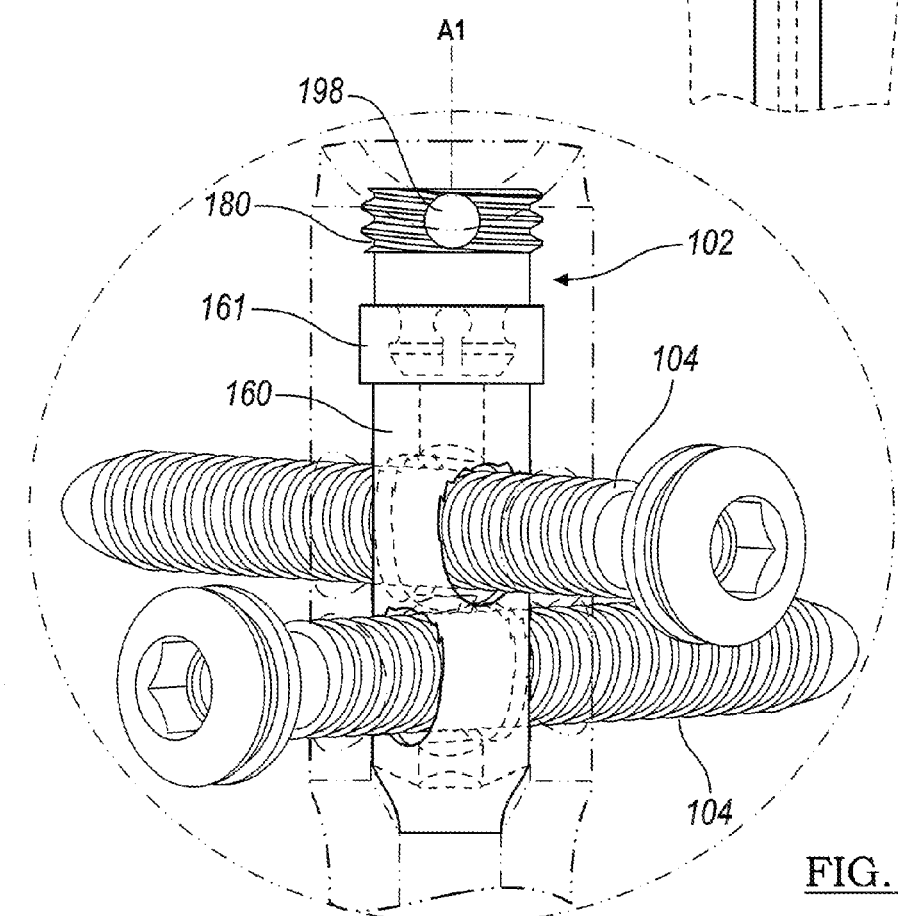
FIG. 17B is an enlarged detail of FIG. 17A.

Referring to FIGS. 15-16, aspects of a tibial securing device 200 and its insertion into a tibial intramedullary implant 102, as discussed above, are illustrated for tibial procedures. The tibial movable member 160 can include first, second and third bores 171, 173, 175 transversely oriented relative to the longitudinal axis A1 of the movable member 160, and circumferentially offset relative to one another, as shown in FIGS. 16, 17A, and 17B. The first and second bores 171, 173 can have closed perimeters and receive corresponding interlocking fasteners 104, such as cortical screws that pass through corresponding bores of the tibial intramedullary implant 102 for fixation into the tibia 70, as shown in FIGS. 17A and 17B. The third bore 175 can have an open perimeter defining two opposing legs 169.

Figures 18A, 18B:
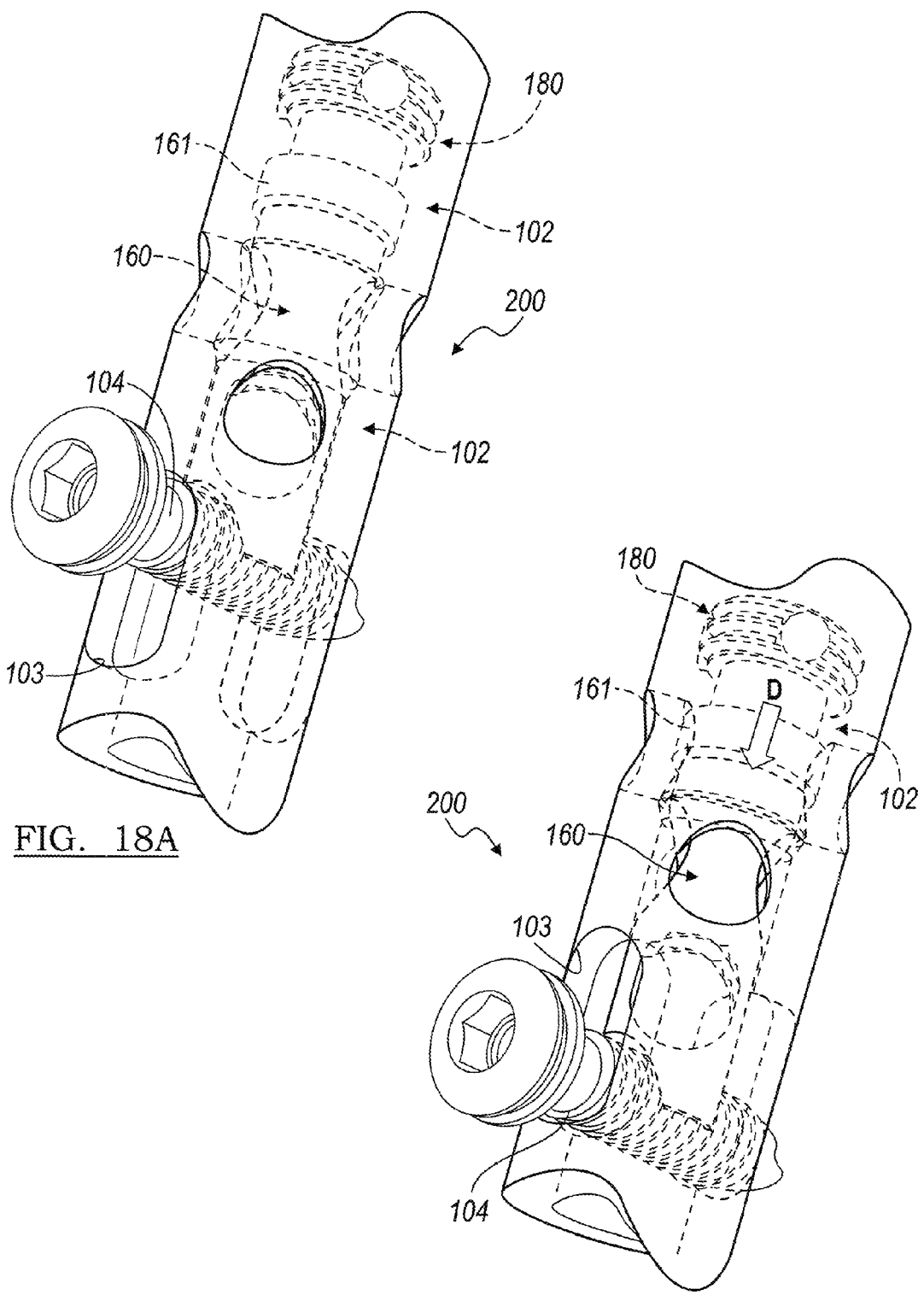
FIG. 18A is a perspective view illustrating a first position of an insert for an intramedullary nail according to the present teachings.
FIG. 18B is a perspective view illustrating a second position of the insert of FIG. 18A.

Referring to FIGS. 18A and 18B, use of the securing device 200 for active compression of fractures is illustrated. An interlocking fastener 104 can pass through the third bore 175 of the movable member 160 and through an elongated slot 103 of the intramedullary implant 102. FIG. 18A illustrates the securing device 200 in a first position that allows dynamic movement along the slot 103. FIG. 18B illustrates the securing device 200 in a second position, in which the fastener 104 engages the distal wall of the slot 103. The movable member 160 can be moved from the first to the second position by rotation of the locking member 180, such that the locking member 180 threadably moves relative to the intramedullary implant 102 and forces the movable member 160 to move distally in the direction of arrow D relative to the intramedullary implant 102.

Figure 19A:
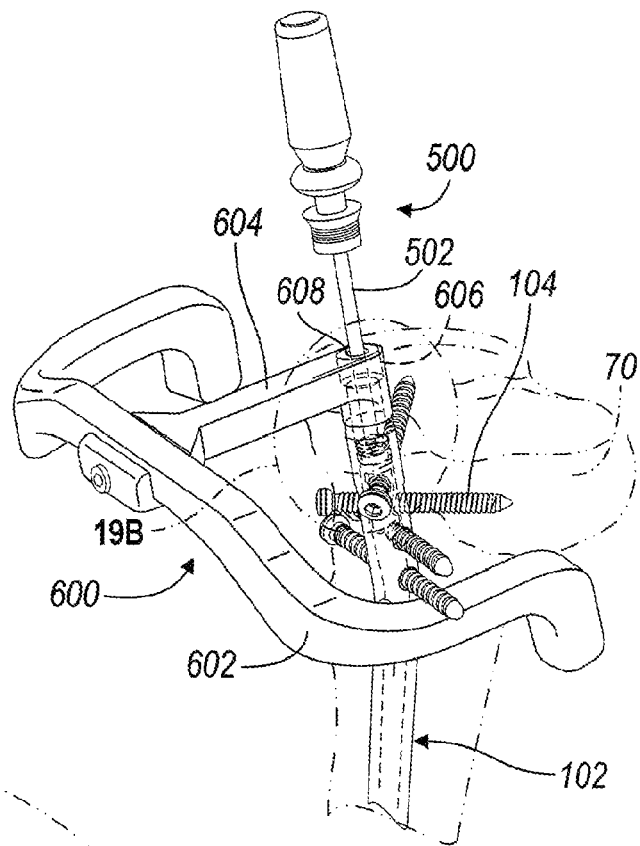
FIG. 19A is a perspective view illustrating instruments for engaging and disengaging an insert for an intramedullary nail according to the present teachings.
Figure 19B:
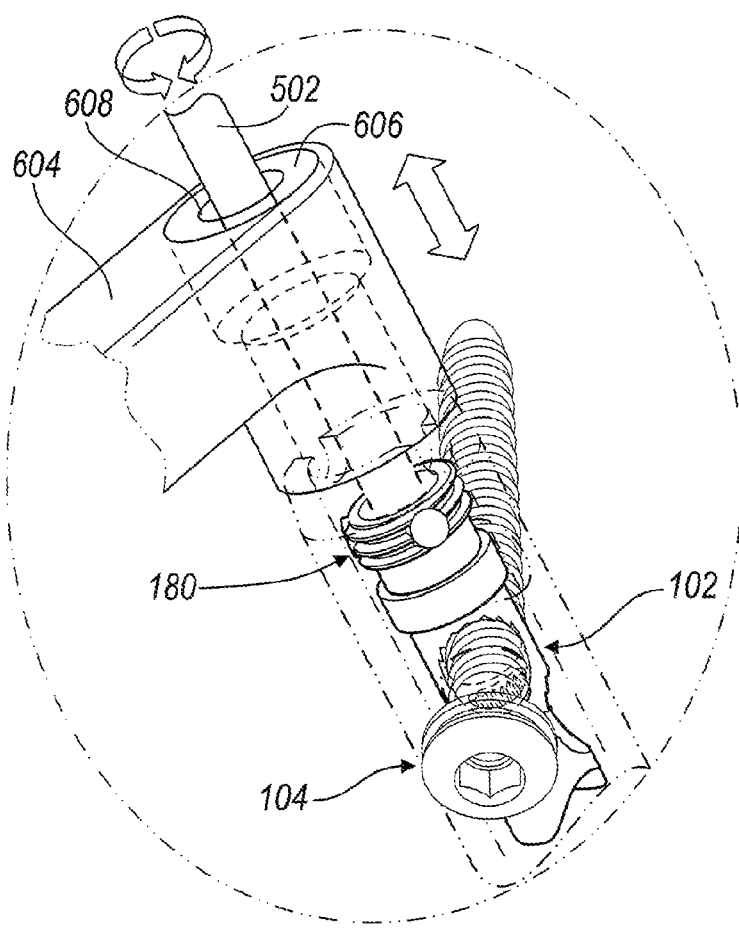
FIG. 19B is an enlarged detail of FIG. 19A.

Referring to FIGS. 19A and 19B, a targeting device 600 for engagement/disengagement of the securing device 200 is illustrated. The targeting device 600 can include a radiolucent targeting arm 602, a driving handle 604 and a cannulated connecting bolt 606 that connects the targeting device 600 to the intramedullary implant 102. A driver 500 with a flexible driving shaft 502 can pass through the bore 608 of the connecting bolt 606 and engage the driver engagement formations 194 of the locking member 180. Rotating the driver shaft 502 clockwise or counterclockwise rotates the locking member 180 correspondingly, and correspondingly urges the movable member 160 distally to a position of engagement with the interlocking fasteners 104, or proximally to a position of disengagement. It will be appreciated, however, that any interlocking fastener 104 can be removed by rotating the interlocking fastener 104, such that the threaded shaft 108 of the interlocking fastener 104 moves relative to the ridges 178 of the corresponding bore of the movable member 160, while the securing device 200 remains in its locked position relative to the intramedullary implant 102.

As it will be appreciated from the above description and drawings, the present teachings provide a securing device for intramedullary implant fixation that can be used telescopically to lock the intramedullary implant with more than one bone fasteners in interlocking or reconstructive procedures for the femur and tibia. Further, active compression of a fracture site can be obtained with the same securing device. Although a few representative applications have been described in detail, it will be understood that the present teachings can be applied to other intramedullary fixation procedures and that features and elements of the fixation device described in connection with one embodiment or procedure can be selectively combined with and/or replace features described in connection with another embodiment or procedure.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. An orthopedic device comprising:
    an intramedullary implant defining a longitudinal bore and a plurality of fastener bores transverse to the longitudinal bore;
    a fastener receivable in one of the plurality of fastener bores, the fastener including threads; and
    a securing device receivable within and movable relative to the longitudinal bore between an unlocked fastener disengagement position and a locked fastener engagement position, the securing device having a guiding bore for allowing the fastener to pass therethrough, the guiding bore having a plurality of engagement formations formed only on a portion of the guiding bore that cooperate with the threads of the fastener such that the plurality of engagement formations enable the fastener to move relative to the securing device when the securing device is in the locked fastener engagement position,
    wherein a bottom surface of the guiding bore is smooth.

2. The orthopedic device of claim 1, wherein the securing device comprises a movable member that defines the guiding bore and a locking member threadably engageable to the longitudinal bore and couplable to the movable member, such that rotation the locking member telescopically moves the movable member within the longitudinal bore.

3. The orthopedic device of claim 2, wherein the locking member includes a resilient portion defining a flange engaging an internal groove of the movable member.

4. The orthopedic device of claim 3, wherein the locking member is cannulated and includes internal driver engagement formations.

5. The orthopedic device of claim 4, wherein the locking member includes a thread-interrupting opening and a thread lock receivable in the opening.

6. The orthopedic device of claim 1, wherein the movable member includes a proximal outer surface having an elongated cross-section and mateably receivable within a proximal inner surface of the longitudinal bore.

7. The orthopedic device of claim 6, wherein the elongated cross-section is substantially elliptical.

8. The orthopedic device of claim 1, wherein the guiding bore further comprises at least first and second guiding bores defining intersecting axes.

9. The orthopedic device of claim 8, wherein the guiding bore further comprises a third guiding bore substantially parallel to one of the first and second axes.

10. The orthopedic device of claim 1, wherein the guiding bore further comprises at least first and second guiding bores circumferentially offset relative to one another.

11. The orthopedic device of claim 1, wherein the intramedullary implant includes an elongated compression slot for a corresponding bone fastener and the guiding bore is aligned with the compression slot, such that the securing device can be selectively moved between positions that allow or disallow movement of the fastener relative to the compression slot.

12. An orthopedic device comprising:
   an intramedullary implant defining a longitudinal bore and a plurality of fastener bores;
   a plurality of bone fasteners receivable in corresponding fastener bores; and
   a securing device defining a plurality of guiding bores, with at least one of the plurality of guiding bores partially enclosed by the securing device and having an opening with an open perimeter such that the opening is defined between a pair of downwardly extending legs of the securing device, the securing device receivable in the longitudinal bore such that the plurality of guiding bores coincide with the plurality of fastener bores for receipt of the plurality of bone fasteners, the securing device movable within the longitudinal bore between a first position that secures at least two bone fasteners to the intramedullary implant, and a second position that disengages the two bone fasteners from the intramedullary implant,
   wherein the securing device includes a locking member and a movable member that defines the plurality of guiding bores, the locking member including a resilient portion couplable to the movable member and a threaded portion threadably couplable to a proximal portion of the longitudinal bore.

13. The orthopedic device of claim 12, wherein at least one bone fastener includes a shaft slidably movable within a sleeve.

14. The orthopedic device of claim 12, wherein at least one bone fastener is engageable or disengageable with a plurality of engagement features formed along at least one of the plurality of guiding bores of the securing device.

15. An orthopedic device comprising:
   an intramedullary implant defining a longitudinal bore and at least first and second fastener bores transverse to the longitudinal bore;
   at least first and second of bone fasteners receivable in the corresponding first and second fastener bores;
   a movable member defining at least first and second guiding bores for receiving the first and second fasteners, a portion of the second guiding bore having an open perimeter such that the second guiding bore is only partially enclosed by the movable member, the movable member movable within the longitudinal bore between a first position that secures the first and second bone fasteners to the intramedullary implant, and a second position that disengages the first and second bone fasteners from the intramedullary implant and the movable member; and
   a locking member having an externally threaded portion threadably engageable to a threaded portion of the longitudinal bore, the locking member having a resilient portion couplable to the movable member.

16. The orthopedic device of claim 15, wherein the intramedullary implant and the movable member are keyed with mateable proximal non circular surfaces.

17. The orthopedic device of claim 15, wherein at least one of the first and second guiding bores include ridge formations for removably securing a corresponding one of the first and second fasteners to the movable member without disengaging the locking member from the intramedullary implant.

18. An orthopedic device comprising:
   an intramedullary implant defining a longitudinal bore;
   at least one bone fastener defining a plurality of threads; and
   a securing device movable within the longitudinal bore between a locked position that engages the at least one bone fastener to the intramedullary implant, and an unlocked position that disengages the at least one bone fastener from the intramedullary implant, the securing device including at least one guiding bore having a plurality of opposed engagement formations separated by a smooth surface that are engageable with the plurality of threads formed on the at least one bone fastener to enable the at least one bone fastener to move relative to the securing device while the securing device is in the locked position.

19. The orthopedic device of claim 18, wherein the at least one bone fastener comprises first and second bone fasteners and the at least one guiding bore comprises first and second guiding bores.

20. An orthopedic device comprising:
   an intramedullary implant defining a longitudinal bore along a longitudinal axis and at least a first transverse bore orientated along a first axis transverse to the longitudinal axis and a second transverse bore orientated along a second axis transverse to the longitudinal axis; and
   a securing device defining at least a first guiding bore along a first guiding axis and a second guiding bore along a second guiding axis that intersects the first guiding axis, the first guiding bore and the second guiding bore having a common opening for receipt of the at least one bone fastener, the securing device receivable within the longitudinal bore such that the first axis of the first transverse bore substantially coincides with the first guiding axis and the second axis of the second transverse bore substantially coincides with the second guiding axis for receipt of at least one bone fastener, the securing device movable relative to the longitudinal bore between a locked fastener engagement position and an unlocked fastener disengagement position,
   wherein at least one of the first guiding bore and the second guiding bore include a first plurality of engagement formations formed opposite a second plurality of engagement formations with a smooth surface defined between the first plurality of engagement formations and second plurality of engagement formations.

21. The orthopedic device of claim 20, wherein the first axis intersects the second axis.

22. The orthopedic device of claim 20, wherein the securing device further comprises a third guiding bore along a third guiding axis, the third guiding axis parallel to one of the first guiding axis and the second guiding axis.

23. The orthopedic device of claim 20, wherein at least a portion of the second guiding bore is defined by an opening having an open perimeter.

24. The orthopedic device of claim 20, wherein the plurality of engagement formations have a generally triangular cross-section.

* * * * *

UNITED STATES PATENT AND TRADEMARK OFFICE
CERTIFICATE OF CORRECTION

PATENT NO. : 8,303,590 B2
APPLICATION NO. : 11/627575
DATED : November 6, 2012
INVENTOR(S) : Timothy M. Elghazaly et al.

It is certified that error appears in the above-identified patent and that said Letters Patent is hereby corrected as shown below:

Column 1,
Lines 35-36, replace "from to the" with --from the--

Column 1,
Line 41, after "second" delete "of"

Column 1,
Line 49, after "from" delete "to"

Column 1,
Line 54, replace "provide" with --provides--

Column 1,
Line 60, after "from" delete "to"

Column 2,
Line 21, after "FIG. 3" insert --;--

Column 2,
Line 22, replace "view" with --views--

Column 2,
Line 25, replace "if" with --of--

Column 3,
Line 24, replace "tibia" with --tibial--

Column 3,
Line 42, after "200" delete "device"

Signed and Sealed this
Twelfth Day of February, 2013

Teresa Stanek Rea
*Acting Director of the United States Patent and Trademark Office*

CERTIFICATE OF CORRECTION (continued)
U.S. Pat. No. 8,303,590 B2

Column 3,
Line 44, after "200" delete "device"

Column 4,
Line 5, replace "opening" with --openings--

Column 4,
Line 61, replace "opening" with --openings--

Column 5,
Lines 15-16, replace "opening fourth 176" with --fourth opening 176--

Column 5,
Line 17, replace "fourth and third openings 174, 176" with --third and fourth openings 174, 176--

Column 6,
Line 47, replace "304, 304', 304''" with --304, 304' 304"--

Column 7,
Line 9, replace "can be also be" with --can also be--

Column 8,
Line 42, after "rotation" insert --of--